(12) United States Patent
Deng et al.

(10) Patent No.: US 11,918,695 B2
(45) Date of Patent: *Mar. 5, 2024

(54) TOPICAL FORMULATION OF HYPERBRANCHED POLYMER-COATED PARTICLES

(71) Applicant: Yale University, New Haven, CT (US)

(72) Inventors: Yang Deng, Edison, NJ (US); Asiri Ediriwickrema, Cary, NC (US); William M. Saltzman, New Haven, CT (US); Michael Girardi, Madison, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/573,807

(22) PCT Filed: May 11, 2016

(86) PCT No.: PCT/US2016/031879
§ 371 (c)(1),
(2) Date: Nov. 13, 2017

(87) PCT Pub. No.: WO2016/183209
PCT Pub. Date: Nov. 17, 2016

(65) Prior Publication Data
US 2018/0256480 A1    Sep. 13, 2018

Related U.S. Application Data

(63) Continuation-in-part of application No. 15/309,741, filed as application No. PCT/US2015/030169 on May 11, 2015, which is a continuation-in-part of application No. 15/309,733, filed as application No. PCT/US2015/030187 on May 11, 2015.

(60) Provisional application No. 62/232,734, filed on Sep. 25, 2015, provisional application No. 62/260,028, filed on Nov. 25, 2015, provisional application No. 61/991,025, filed on May 9, 2014.

(30) Foreign Application Priority Data

May 11, 2015  (WO) ................ PCT/US2015/030169
May 11, 2015  (WO) ................ PCT/US2015/030187

(51) Int. Cl.
*A61K 31/337* (2006.01)
*A61K 8/02* (2006.01)
(Continued)

(52) U.S. Cl.
CPC .......... *A61K 9/5153* (2013.01); *A61K 8/0241* (2013.01); *A61K 8/11* (2013.01); *A61K 8/345* (2013.01); *A61K 8/8147* (2013.01); *A61K 8/86* (2013.01); *A61K 8/922* (2013.01); *A61K 9/0019* (2013.01); *A61K 9/5031* (2013.01); *A61K 31/00* (2013.01); *A61K 31/7076* (2013.01); *A61K 47/6935* (2017.08); *A61K 47/6937* (2017.08); *A61P 35/00* (2018.01); *A61Q 17/005* (2013.01); *A61Q 17/04* (2013.01); *A61Q 19/00* (2013.01); *A61K 2800/624* (2013.01); *A61K 2800/654* (2013.01)

(58) Field of Classification Search
CPC ........ A61K 2800/624; A61K 2800/654; A61K 31/00; A61K 31/7076; A61K 47/6935; A61K 47/6937; A61K 8/0241; A61K 8/11; A61K 8/345; A61K 8/8147; A61K 8/86; A61K 8/922; A61K 9/0019; A61K 9/5031; A61K 9/5153; A61Q 17/005; A61Q 17/04; A61Q 19/00; A61P 35/00
USPC ...................................................... 424/401
See application file for complete search history.

(56) References Cited

U.S. PATENT DOCUMENTS 3,266,987 A   8/1966   Crowley
3,832,253 A   8/1974   Palma
(Continued)

FOREIGN PATENT DOCUMENTS

GB    929401      6/1963
WO    93012096    6/1993
(Continued)

OTHER PUBLICATIONS

X. Gai et al., 2009, Journal of Controlled Release, 140, pp. 141-147.*
(Continued)

*Primary Examiner* — Alma Pipic
(74) *Attorney, Agent, or Firm* — PABST PATENT GROUP LLP

(57) ABSTRACT

Core-shell particles have a hydrophobic core and a shell formed of o containing hyperbranched polymers (HP). The HP can be covalently bound to the one or more materials that form the core or coated thereon. The HP coating can be modified to adjust the properties of the particles. For example, unmodified HP coatings resist non-specific protein absorption. Alternatively, the hydroxyl groups on the HP coating can be chemically modified to form functional groups that react with functional groups on tissue to adhere the particles to the tissue, cells, or extracellular materials, such as proteins. Such functional groups include, but not limited to, aldehydes, amines, and O-substituted oximes. Topical formulation for application to the skin contain these HP coated nanoparticles. In some embodiments, the particles include cosmetic, therapeutic, diagnostic, nutraceutical, and/or prophylactic agents, such as those used as sunblock compositions.

10 Claims, 10 Drawing Sheets

(51) Int. Cl.
- *A61K 8/11* (2006.01)
- *A61K 8/34* (2006.01)
- *A61K 8/81* (2006.01)
- *A61K 8/86* (2006.01)
- *A61K 8/92* (2006.01)
- *A61K 9/00* (2006.01)
- *A61K 9/50* (2006.01)
- *A61K 9/51* (2006.01)
- *A61K 31/00* (2006.01)
- *A61K 31/7076* (2006.01)
- *A61K 47/69* (2017.01)
- *A61P 35/00* (2006.01)
- *A61Q 17/00* (2006.01)
- *A61Q 17/04* (2006.01)
- *A61Q 19/00* (2006.01)

(56) References Cited

U.S. PATENT DOCUMENTS

| | | |
|---|---|---|
| 3,854,480 A | 12/1974 | Zaffaroni |
| 3,960,757 A | 6/1976 | Morishita |
| 4,452,775 A | 6/1984 | Kent |
| 4,460,563 A | 7/1984 | Calanchi |
| 4,667,013 A | 5/1987 | Reichle |
| 4,675,189 A | 6/1987 | Kent |
| 4,714,680 A | 12/1987 | Civin |
| 4,748,034 A | 5/1988 | Rham |
| 4,794,000 A | 12/1988 | Ecanow |
| 4,883,666 A | 11/1989 | Sabel |
| 4,965,204 A | 10/1990 | Civin |
| 5,034,506 A | 7/1991 | Summerton |
| 5,061,620 A | 10/1991 | Tsukamoto |
| 5,075,109 A | 12/1991 | Tice |
| 5,114,719 A | 5/1992 | Sabel |
| 5,118,528 A | 6/1992 | Fessi |
| 5,133,974 A | 7/1992 | Paradissis |
| 5,239,660 A | 8/1993 | Ooi |
| 5,356,802 A | 10/1994 | Chandrasegaran |
| 5,407,686 A | 4/1995 | Patel |
| 5,422,251 A | 6/1995 | Fresco |
| 5,436,150 A | 7/1995 | Chandrasegaran |
| 5,487,994 A | 1/1996 | Chandrasegaran |
| 5,527,675 A | 6/1996 | Coull |
| 5,539,082 A | 7/1996 | Nielsen |
| 5,601,835 A | 2/1997 | Sabel |
| 5,623,049 A | 4/1997 | Lobberding |
| 5,643,741 A | 7/1997 | Tsukamoto |
| 5,677,136 A | 10/1997 | Simmons |
| 5,698,546 A | 12/1997 | Bridger |
| 5,714,331 A | 2/1998 | Buchardt |
| 5,716,827 A | 2/1998 | Tsukamoto |
| 5,736,152 A | 4/1998 | Dunn |
| 5,736,336 A | 4/1998 | Buchardt |
| 5,750,397 A | 5/1998 | Tsukamoto |
| 5,759,793 A | 6/1998 | Schwartz |
| 5,773,571 A | 6/1998 | Nielsen |
| 5,786,571 A | 7/1998 | Bethel |
| 5,945,337 A | 8/1999 | Brown |
| 5,962,426 A | 10/1999 | Glazer |
| 6,140,081 A | 10/2000 | Barbas |
| 6,143,211 A | 11/2000 | Mathiowitz |
| 6,261,841 B1 | 7/2001 | Cohen |
| 6,303,376 B1 | 10/2001 | Glazer |
| 6,383,500 B1 * | 5/2002 | Wooley .......... A61P 43/00 424/401 |
| 6,453,242 B1 | 9/2002 | Eisenberg |
| 6,534,261 B1 | 3/2003 | Cox |
| 6,610,512 B1 | 8/2003 | Barbas |
| 6,673,545 B2 | 1/2004 | Faris |
| 6,677,157 B1 | 1/2004 | Cohen |
| 6,699,475 B1 | 3/2004 | Panicali |
| 6,746,838 B1 | 6/2004 | Choo |
| 6,866,997 B1 | 3/2005 | Choo |
| 6,919,208 B2 | 7/2005 | Levy |
| 7,067,617 B2 | 6/2006 | Barbas |
| 7,078,389 B2 | 7/2006 | Glazer |
| 7,279,463 B2 | 10/2007 | Glazer |
| 7,534,448 B2 | 5/2009 | Saltzman |
| 7,534,449 B2 | 5/2009 | Saltzman |
| 7,550,154 B2 | 6/2009 | Saltzman |
| 7,566,535 B2 | 7/2009 | Kmiec |
| 8,206,747 B2 | 6/2012 | Zale |
| 8,309,356 B2 | 11/2012 | Glazer |
| 8,658,608 B2 | 2/2014 | Glazer |
| 8,715,736 B2 | 5/2014 | Sachdeva |
| 8,889,117 B2 | 11/2014 | Mellman |
| 9,492,382 B2 | 11/2016 | Holger |
| 9,492,400 B2 * | 11/2016 | Jon .......... A61K 9/5138 |
| 2002/0165356 A1 | 11/2002 | Barbas |
| 2003/0044978 A1 | 3/2003 | Young |
| 2003/0148352 A1 | 8/2003 | Glazer |
| 2004/0197892 A1 | 10/2004 | Moore |
| 2005/0019303 A1 | 1/2005 | Tsai |
| 2005/0055078 A1 | 3/2005 | Campbell |
| 2005/0118252 A1 | 6/2005 | Bae |
| 2006/0105026 A1 * | 5/2006 | Fortune .......... A61L 15/225 424/443 |
| 2007/0154989 A1 | 7/2007 | Barbas |
| 2007/0213269 A1 | 9/2007 | Barbas |
| 2008/0050920 A1 | 2/2008 | Kawahara |
| 2009/0155371 A1 * | 6/2009 | Sojka .......... A61K 8/27 424/497 |
| 2009/0239789 A1 | 9/2009 | Saltzman |
| 2009/0269397 A1 | 10/2009 | Saltzman |
| 2009/0312402 A1 | 12/2009 | Contag |
| 2010/0151436 A1 | 6/2010 | Fong |
| 2010/0172882 A1 | 7/2010 | Glazer |
| 2011/0008451 A1 | 1/2011 | Saltzman |
| 2011/0045092 A1 | 2/2011 | Livney |
| 2011/0060036 A1 | 3/2011 | Nie |
| 2011/0200666 A1 * | 8/2011 | Teichmuller .......... A61K 8/14 424/450 |
| 2011/0262406 A1 | 10/2011 | Campo |
| 2011/0268810 A1 | 11/2011 | Saltzman |
| 2011/0293585 A1 | 12/2011 | Del Campo |
| 2012/0195957 A1 | 8/2012 | Sachdeva |
| 2014/0342003 A1 | 11/2014 | Saltzman |
| 2015/0073041 A1 | 3/2015 | Saltzman |
| 2015/0118311 A1 | 4/2015 | Zhou |
| 2015/0125384 A1 | 5/2015 | Mellman |
| 2016/0263875 A1 | 9/2016 | Ueno |

FOREIGN PATENT DOCUMENTS

| | | |
|---|---|---|
| WO | 95001364 | 1/1995 |
| WO | 9602558 | 2/1996 |
| WO | 96039195 | 2/1996 |
| WO | 96040271 | 12/1996 |
| WO | 96040898 | 12/1996 |
| WO | 98053059 | 11/1998 |
| WO | 00050900 | 8/2000 |
| WO | 2002010142 | 2/2002 |
| WO | 2003016496 | 2/2003 |
| WO | 2003052071 | 6/2003 |
| WO | 2005108622 | 11/2005 |
| WO | 2008086529 | 7/2008 |
| WO | 2009/123934 | 10/2009 |
| WO | 2009123934 | 10/2009 |
| WO | 2010123983 | 10/2010 |
| WO | 2011053989 | 5/2011 |
| WO | 2011072246 | 6/2011 |
| WO | 2011133802 | 10/2011 |
| WO | 2011133803 | 10/2011 |
| WO | 2012085554 | 6/2012 |
| WO | 2012151539 | 11/2012 |
| WO | 2012156094 | 11/2012 |
| WO | 2013082529 | 6/2013 |
| WO | 2013166487 | 11/2013 |
| WO | 2013176772 | 11/2013 |
| WO | 2014018423 | 6/2014 |
| WO | 2014110020 | 7/2014 |
| WO | 2015148716 | 10/2015 |

(56) References Cited

FOREIGN PATENT DOCUMENTS

| WO | 2015172149 | 11/2015 |
|----|------------|---------|
| WO | 2015172153 | 11/2015 |
| WO | 2016183209 | 11/2016 |
| WO | 2016183217 | 11/2016 |

OTHER PUBLICATIONS

Alshamsan, "Nanoprecipitation is more efficient than emulsion solvent evaporation method to encapsulate cucurbitacin I in PLGA nanoparticles", Saudi Pharmaceutical Journal, 22(3):219-222 (2014).
Bao, et al., "OX26 modified hyperbranched polylycerol-conjugated poly(lactic-co-glycolic acid) nanoparticles: synthesis characterization and evaluation of its brain delivery ability", J Mater Sci Mater Med., 23(8):1891-901 (2012).
Barbero, et al., "Pig and guinea pig skin as surrogates for human in vitro penetration studies: a quantitative review", Toxicol. In Vitro 23:1-13 (2009).
Barnard, "One-to-one comparison of sunscreen efficacy, aesthetics and potential nanotoxicity", Nature Nanotech., 5:271-4 (2010).
Bastien, et al., "The sunscreen agent 2-phenylbenzimidazole-5-sulfonic acid photosensitizes the formation of oxidized guanines in cellulo after UV-A or UV-B exposure", J Invt Dermatol, 130:2463-71 (2010).
Beck, et al., "New long-acting injectable microcapsule contraceptive system", Am. J Obstet. Gynecol., 135(3) (1979a).
Beck, et al., "A new long-acting injectable microcapsule system for the administration of progesterone", Fertil. Steril., 31:545 (1979b).
Benita, et al., "Characterization of drug-loaded poly(d,I-lactide) microspheres", J. Pharm. Sci., 73:1721 (1984).
Bourges, et al., "Ocular drug delivery targeting the retina and retinal pigment epithelium using polylactide nanoparticles", Invest. Ophthalmol. Vis Sci., 44:3562-9 (2003).
Cheng, et al., A holistic approach to targeting disease with polymeric nanoparticles, Nat Rev Drug Discov, 14:239-247 (2015).
Deng, et al., "A sunblock based on bioadhesive nanoparticles", Nat Mater., 14(12):1278-85 (2015).
Deng, et al., "Improved i.p. drug delivery with bioadhesive nanoparticle", PNAS, 113(41): 11453-8 (2016).
Deng, et al., "The effect of hyperbranched polyglycerols coatings on drug delivery using degradable polymer nanoparticles", Biomaterials, 35:6595-6602 (2014).
Dong, et al., "Poly(glycoamidoamine) brushes formulated nanomaterials for systemic siRNA and mRNA delivery in vivo", Nano Lett, 16:842-8 (2016).
Federman, et al., "Sunscreen counseling by US physicians", JAMA 312:87-8 (2014).
Ferrari, et al., "Nanoparticle therapeutics: FDA approval, clinical trials, regulatory pathways, and case study", Nat Rev Cancer, 5:161-171 (2005).
Gao et al., "Hyperbranched polymers: from synthesis to applications". Prog. Polym. Sci. 29:183-275 (2004).
Gao, "Overcoming the blood-brain barrier for delivering drugs into the brain by using adenosine receptor nanoagonist", ACS Nano, 8(4):3678-3689 (2014).
Gao, et al., "Synthesis and physicochemical characterization of a novel amphiphilic polylactic acid- hyperbranched polyglycerol conjugate for protein delivery", J Controled Release, 140:141-7 (2009).
Gaudin, et al., "Poly(Lacticacid)—☐Hyperbranched Polyglycerol Nanopar4cles for Improved Drug Treatment of Gliomas by Convec4on—☐Enhanced Delivery", Sno-Scidot Joint Conference on Therapeutic Delivery to the CNS, Marriot Rivercenter Hotel, San Antonio, TX Nov. 18-19 (2015).
Gerweck, et al., "Cellular pH gradient in tumor versus normal tissue: potential exploitation for the treatment of cancer.", Cancer Res 56: 1194-1198 (1996).
Gilchrest, "Photoaging", The Journal of Investigative Dermatology 133:E2-6 (2013).

Girard, et al., "UVA-induced damage to DNA and proteins: direct versus indirect photochemical processes", J Phys Conf Ser. 261 (2011).
Gref, et al., "The controlled intravenous delivery of drugs using PEG-coated sterically stabilized nanospheres", Adv Drug Deliv Rev, 16:215-233 (1995).
Gu et al., "Topical permeation enhancers efficiently deliver polymer micro and nanoparticles to epidermal Langerhans' cells", J Drug Deliv Sci Tec., 14:265-73 (2004).
Gu, et al. "Precise engineering of targeted nanoparticles by using self-assembled biointegrated block copolymers", PNAS, 105:2586-91 (2008).
Gulston et al., "Illumination of human keratinocytes in the presence of the sunscreen ingredient Padimate-O and through an SPF-15 sunscreen reduces direct photodamage to DNA but increases strand breaks", Mutat Res-Gen Tox En 444:49-60 (1999).
Guzman, et al., "Local intraluminal infusion of biodegradable polymeric nanoparticles. A novel approach for prolonged drug delivery after balloon angioplasty", Circulation 94:1441-8 (1996).
Han, et al., "Polymorphisms in DNA double-strand break repair genes and skin cancer risk", Cancer Res. 64:3009-3013 (2004).
Hanson, et al., "Sunscreen enhancement of UV-induced reactive oxygen species in the skin", Free RadicBiol Med, 41:1205-12 (2006).
Harris, et al., "Effect of pegylation on pharmaceuticals", Nat Rev Drug Discov, 2:214-221 (2003).
Hayden, et al., "Sunscreen penetration of human skin and related keratinocyte toxicity after topical application", Skin Pharmacol. Physiol. 18:170-4 (2005).
Hayden, et al., "Systemic absorption of sunscreen after topical application", Lancet, 350:863-4 (1997).
International Search Report for corresponding PCT application PCT/US2015/030187 dated Aug. 5, 2015.
International Search Report for PCT application PCT/US2015/030169 dated Aug. 4, 2015.
International Search Report for PCT application PCT/US2016/031879 dated Jul. 22, 2016.
International Search Report for PCT application PCT/US2016/031890 dated Jul. 22, 2016.
Kimura, et al., "Measurement of skin permeation/penetration of nanoparticles for their safety evaluation", Biol. Pharm. Bull. 35:1476-86 (2012).
Krause, et al., "Sunscreens: are they beneficial for health? An overview of endocrine disrupting properties of UV-filters", Int. J. Androl. 35:424-36 (2012).
Labhasetwar, et al., "Arterial uptake of biodegradable nanoparticles: effect of surface modifications", J Pharm Sci 87, 1229-34 (1998).
Lesniak, et al., "Nanoparticle adhesion to the cell membrane and its effect on nanoparticle uptake efficiency", J Am Chem Soc, 135:1438-1444 (2013).
Limoli, et al., "UV-induced replication arrest in the xeroderma pigmentosum variant leads to DNA double-strand breaks, gamma-H2AX formation, and Mre11 relocalization", PNAS. 99:233-8 (2002).
Lindqvist, et al., "Avoidance of sun exposure is a risk factor for all-cause mortality: results from the Melanoma in Southern Sweden cohort", J. Intern. Med. 276:77-86 (2014).
Marin, et al., "Critical evaluation of biodegradable polymers used in nanodrugs", Int J Nanomedicine 8, 3071-3090 (2013).
Mitragotri, et al., "Overcoming the challenges in administering biopharmaceuticals: formulation and delivery strategies", Nature Reviews. Drug discovery, 13:655-72 (2014).
Morrison, et al., "High-flow microinfusion: tissue penetration and pharmacodynamics", American Journal of Physiology 266:R292-R305 (1994).
Mugabe, et al., "Paclitaxel incorporated in hydrophobically derivatized hyperbranched polyglycerols for intravesical bladder cancer therapy", BJU Intl., 102:978-86 (2008).
Nance, et al., "A dense poly(ethylene glycol) coating improves penetration of large polymeric nanoparticles within brain tissue", Sci Transl Med, 4(149):149ra119 (2012).

(56) References Cited

OTHER PUBLICATIONS

Pan, et al., "Adverse effects of titanium dioxide nanoparticles on human dermal fibroblasts and how to protect cells", Small, 5:511-20 (2009).
Perugini, et al., "Effect of nanoparticle encapsulation on the photostability of the sunscreen agent, 2-ethylhexyl-p-methoxycinnamate", Int J Pharma., 246:37-45 (2002).
Planta, "Sunscreen and melanoma: is our prevention message correct", J Am Board of Fam Med, JABFM, 24:735-9 (2011).
Quatrano et al., "Current principles of sunscreen use in children", Curr. Opin. Pediatr. 25:122-9 (2013).
Rao, et al., "Polylysine-modified PEG-based hydrogels to enhance the neuro-electrode interface", J. Biomater. Sci. Polym. Ed., 22:611-625 (2011).
Saucier-Sawyer, et al., "Systemic delivery of blood-brain barrier-targeted polymeric nanoparticles enhances delivery to brain tissue", Journal of Drug Targeting, 23(7-8):736-7489 (2015).
Solaro, et al., "Targeted delivery of protein drugs by nanocarriers", Materials, 3:1928-80 (2010).
Song, et al., "Arterial uptake of biodegradable nanoparticles for intravascular local drug delivery: results with an acute dog model", J Control Release 54(2):201-11 (1998).
Stern, et al., "The risk of melanoma in association with long-term exposure to PUVA", J Am Acad Dermatol, 44:755-761 (2001).
Tanner, "Sunscreen product formulation", Dermatologic Clinics, 24:53-62 (2006).
Tatokoro, et al., "heat shock protein 90 targeting therapy: state of the art and future perspective", ESCLI J., 14:48-58 (2015).
Thompson et al., "The cancer therapeutic potential of Chk1 inhibitors: how mechanistic studies impact on clinical trial design", Br J Clin Pharmacol., 76(3): 358-369 (2013).
Trouiller, et al., "Titanium dioxide nanoparticles induce DNA damage and genetic instability in vivo in mice", Cancer Res. 69:8784-9 (2009).
Vemula, et al., "Nanoparticles reduce nickel allergy by capturing metal ions.", Nature Nanotech., 6:291-5 (2011).
Walkey, et al., "Nanoparticle size and surface chemistry determine serum protein adsorption and macrophage uptake", J Am Chem Soc, 134:2139-47 (2012).
Wu, et al., "Toxicity and penetration of TiO2 nanoparticles in hairless mice and porcine skin after subchronic dermal exposure", Toxicol Lett, 191:1-8 (2009).
Yang et al., "A sunblock based on bioadhesive nanoparticles," Nature Materials, 14(12): 1278-1285 (2015).
Yang et al., "The effect of hyperbranched polyglycerol coatings on drug delivery using degradable polymer nanoparticles," Biomaterials, 35(24):6595-6602 (2014A).
Yang, et al., "Intraperitoneal delivery of paclitaxel by poly(ether-anhydride) microspheres effectively suppresses tumor growth in a murine metastatic ovarian cancer model", Drug DelivTranslIRe., 4, 203-209 (2014B).
Yeh, et al., "Self-assembled monothiol-terminated hyperbranched polyglycerols on a gold surface: a comparative study on the structure, morphology, and protein adsorption characteristics with linear poly(ethylene glycol)s.", Langmuir. 24(9):4907-16(2008).
Zakrewsky, et al., "Ionic liquids as a class of materials for transdermal delivery and pathogen neutralization", PNAS., 111:13313-8 (2014).
Zeng, et al., "Cholic acid-functionalized nanoparticles of star-shaped PLGA-vitamin E Tpcs copolymer for docetaxel delivery to cervical cancer", Biomaterials, 14:6058-67 (2013),.
Zheng, et al., "Topical delivery of siRNA-based spherical nucleic acid nanoparticle conjugates for gene regulation", PNAS, 109:11975-80 (2012).
Andreev, et al., "pH-sensitive membrane peptides (pHILPs) as a novel class of delivery agents", Molecular Brain Biology, 2(7):341-352 (2010).
Nag, et al., "Surface Engineering of liposomes for Stealth Behavior", Pharmaceutics, 5:542-569 (2013).
Bao et al., "QX26 modified hyperbranched polyglyceryl-conjugated poly(lactic-co-glycolic acid) nanoparticles: synthesis, characterization and evaluation of its brain delivery ability", Journal of Materials Science: Materials in Medicine, 23(8): 1891-1901 (2012).
Charlton, et al., "Evaluation of bloadhesive polymers as delivery systems for nose to brain deliver: in vitro characterization study," Journal of Controlled Release, 118: 225-234 (2007).
Li, et al., "Stealth nanoparticles: High density but sheddable PEG is a key for tumor targeting", Journal of Controlled Release, 145(3): 178-181 (2010).
Nagasaki, et al., "The Reactive Polymeric Micelle Based on An Aldehyde-Ended Poly(ethylene glycol/Poly(lactide) Block Copolymer", American Chemical Society, Macromolecules, 31(5): 1473-1479 (1998).
Yang, et al., "Design Strategies and Applications of Tissue Bioadhesives," Macromolecular Bioscience, 13(3): 271-288 (2013).
Charlton, et al., "Evaluation of bioadhesive polymers as delivery systems for nose to brain deliver: in vitro characterization study," *Journal of Controlled Release*, 118: 225-234 (2007).
Artzi, et al., "Aldehyde-Amine Chemistry Enables Modulated Biosealants with Tissue-Specific Adhesion", Advanced Materials, 21:3399-3403 (2009).
Artzi, et al., "Aldehyde-Amine Chemistry Enables Tissue Adhesive Materials to Respond to Physiologic Variation and Pathologic States", Isr. J. Chem., 53: 748-755 (2013).
Feldborg, et al., "Quantitative Evaluation of Bioorthogonal Chemistries for surface Functionalization of Nanoparticles", Bioconjugate Chem. 23:2444-2450 (2012).
Iha, et al., "Applications of Orthogonal "Click" Chemistries in the Synthesis of Functional Soft Materials", Chem. Rev., 109:5620-5686 (2009).
Liu, et al., "pH-sensitive nano-systems for drug delivery in cancer therapy", Biotechnology Advances, 32: 693-710 (2014).
Perlikowska, et al., "Bioavailability of Endomorhpins and the Blood-brain Barrier—A Review", Medicinal Chemistry, 10:2-17 (2014).
Romberg, et al., "Sheddable Coatings for Long-Circulating Nanoparticles", Pharmaceutical Research, 25(1):55-71 (2008).
The Merck Index Online , 2 pages retrieved from the internet <https://www.rsc.org/Merck-Index/monograph/print/m5533/formaldehyde?q=authorize>, accessed Feb. 26, 2022.
Vauthier, et al., "Poly(alkylcyanoacrylates) as biodegradable materials for biomedical applications", Advanced Drug Delivery Reviews, 55:519-548 (2003).

* cited by examiner

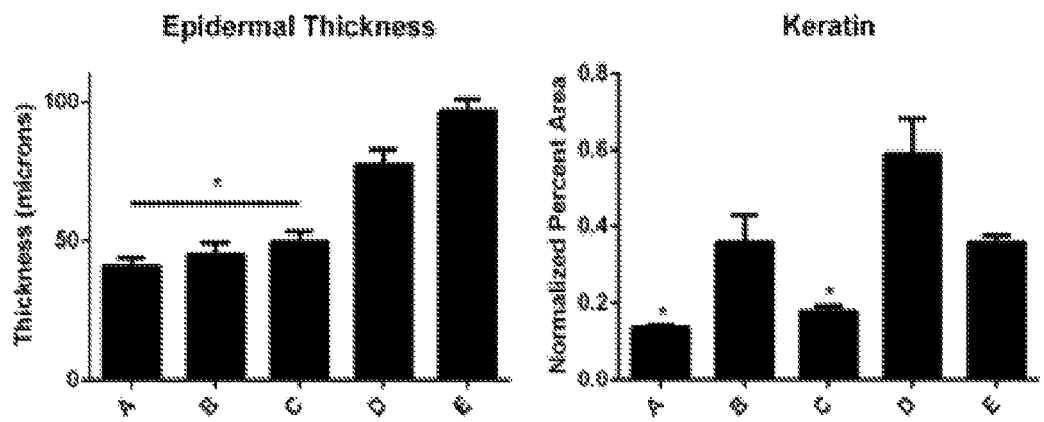
FIG. 7A
FIG. 7B
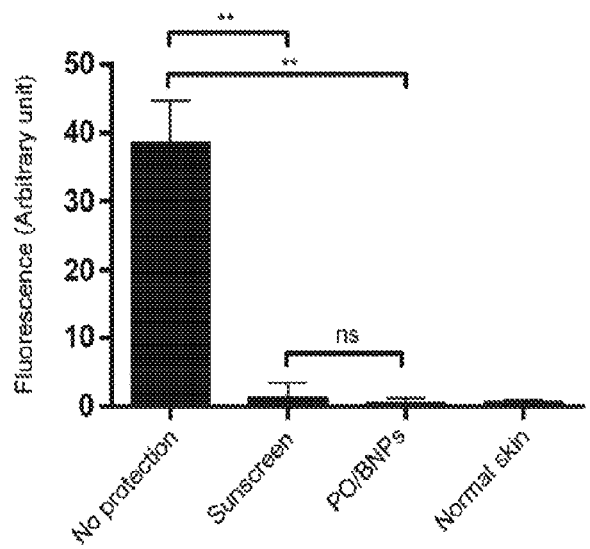
FIG. 8

TOPICAL FORMULATION OF HYPERBRANCHED POLYMER-COATED PARTICLES

CROSS-REFERENCE TO RELATED APPLICATIONS

This application is a 371 application of International Application No. PCT/US2016/031879, filed May 11, 2016, which claims the benefit of and priority to International Application PCT/US2015/030169 filed May 11, 2015, International Application PCT/US2015/030187 filed May 11, 2015, U.S. Provisional Application No. 62/232,734 filed Sep. 25, 2015, and U.S. Provisional Application No. 62/260,028 filed Nov. 25, 2015, the disclosure of each of which are hereby incorporated herein by reference in their entirety. This application is also a continuation-in-part of U.S. application Ser. No. 15/309,741, filed Nov. 8, 2016, which is a 371 application of International Application No. PCT/US2015/030169 filed May 11, 2015, which claims benefit of U.S. Provisional Application 61/991,025 filed May 9, 2014. This application is also a continuation-in-part of U.S. application Ser. No. 15/309,733 filed Nov. 8, 2016, which is a 371 International Application No. PCT/US2015/030187 filed May 11, 2015, which claims the benefit of U.S. Provisional Application No. 61/991,025 filed May 9, 2014.

STATEMENT REGARDING FEDERALLY SPONSORED RESEARCH

This invention was made with government support under Grant Nos. EB000487, CA149128, CA102703 and CA149128 awarded by the National Institutes of Health. The government has certain rights in the invention.

FIELD OF THE INVENTION

This invention is in the field of particles, such as microparticles and/or nanoparticles, coated with hyperbranched polymers, wherein the coating can be tuned to provide stealth or adhesive properties, and formulated for topical use.

BACKGROUND OF THE INVENTION

Ultraviolet (UV) radiation from sunlight can lead to multiple adverse effects including cutaneous phototoxicity (sunburn), photoaging, and carcinogenesis (Federman et al., *JAMA* 312:87-88 (2014); Stern et al, *Journal of the American Academy of Dermatology* 44:755-761 (2001)). UVB directly induces cyclopyrimidine dimers (CPDs) within the genomic DNA (gDNA) of keratinocytes, and both UVA and UVB exposure markedly enhance production of reactive oxidation species (ROS) that damage a variety of cellular components, including gDNA (Gilchrest, B. A. *The Journal of Investigative Dermatology* 133:E2-6 (2013)), and induce immunosuppressive cytokines (Schwarz and Luger, *Journal of Photochemistry and Photobiology. B, Biology* 4:1-13 (1989)). UV-exposure is clearly linked to both melanoma and non-melanoma skin cancer development (Gordon et al, *Facial Polymer Surgery: FPS* 29:402-410 (2013)). Over the past few decades, commercially available UV-protective sunblocks have largely incorporated organic UV filters [e.g. avobenzone, octinoxate, octocrylene, oxybenzone and padimate O (PO) (Hayden et al., *Skin Pharmacol. Physiol.* 18:170-174 (2005)] as formulations based on oil/water emulsions (Quatrano and Dinulos, *Curr. Opin. Pediatr.* 25:122-129 (2013)). There are substantial concerns, however, that these aromatic organic compounds can penetrate through the stratum corneum, or via follicles, into epidermal cells, keratinocytes and Langerhans cells (Hayden et al., *Skin Pharmacol. Physiol.* 18:170-174 (2005)). The potential for systemic absorption of such organic compounds, and their depot in adipose tissue, has also been a concern (Gulston and Knowland, *Mutat Res-Gen Tox En* 444:49-60 (1999); Hanson et al., *Free Radical Biology and Medicine* 41:1205-1212 (2006); Bastien et al., *The Journal of Investigative Dermatology,* 130:2463-2471 (2010); Krause et al., *Int. J. Androl.* 35:424-436 (2012)).

Alternatively, UV-blocking inorganic materials such as micronized zinc oxide (ZnO) and titanium dioxide ($TiO_2$) particles (Barnard, *Nature Nanotechnology,* 5:271-274 (2010)) have been utilized. While transdermal penetration of the inorganic particles appears to be less of a concern than for the organic agents, both types of sunblock agents have shown the capacity to enhance ROS generation after UV exposure, suggesting even small quantities may contribute to cellular damage and ultimately carcinogenesis (Pan et al., *Small,* 5:511-520 (2009); Trouiller et al., *Cancer Res.* 69:8784-8789 (2009); Wu et al., *Toxicology Letters,* 191:1-8 (2009); Zhang et al., *Journal of Biomedical Nanotechnology,* 10:1450-1457 (2014)). Thus, while the application of such products protects against sunburn, e.g. raises the skin's minimal erythema dose (MED), there continues to be controversy regarding their overall effectiveness in preventing skin cancer (Krause et al., *Int. J. Androl.* 35:424-436 (2012); Planta, *Journal of the American Board of Family Medicine: JABFM,* 24:735-739 (2011); Lindqvist et al., *J. Intern. Med.* 276:77-86 (2014); Plourde, E. Sunscreens—Biohazard: Treat As Hazardous Waste. (New Voice Publications (2011)). Moreover, several UV filters have been detected in human urine and breast milk samples after tropical treatment, and may mediate systemic effects including endocrine disruption (Hayden et al., *Skin Pharmacol. Physiol.* 18:170-174 (2005); Krause et al., *Int. J. Androl.* 35:424-436 (2012); Hayden et al., *Lancet,* 350:863-864 (1997)). Therefore, preventing direct skin contact and subsequent epidermal penetration may be essential to eliminating the potential adverse effects of sunscreens.

Some commercially available sunscreens are opaque, due to their use of large particles (Barnard, *Nature Nanotechnology,* 5:271-274 (2010)). The smaller, non-adhesive nanoparticles used in other commercially available sunscreens accumulate in hair follicles or penetrate deep into dermis, causing a variety of adverse effects (Vemula et al., *Nature Nanotechnology,* 6:291-295 (2011); Kimura et al., *Biol. Pharm. Bull.* 35:1476-1486 (2012)). Numerical simulations of nanoparticle properties suggest that unless small nanoparticles can be clearly demonstrated as safe, it is increasingly difficult to solve this paradox (Barnard, *Nature Nanotechnology,* 5:271-274 (2010)). (Mitragotri et al., *Nature Reviews. Drug discovery,* 13:655-672 (2014); Zakrewsky et al., *Proc. Natl. Acad. Sci. U.S.A.* 111:13313-13318 (2014); Zheng et al., *Proc. Natl. Acad. Sci. U.S.A.* 109:11975-11980 (2012); Gu and Roy, *J Drug Deliv Sci Tec.* 14:265-273 (2004)).

Commercial sunscreens polymerize monomers with an initiator in order to stabilize the UV filters into a film that coats the skin. The chemicals involved include a variety of acrylate derivatives and multiple initiators (Nair et al., *Pigment Cell and Melanoma Research* 27:843-845 (2014), which have been implicated in irritant and allergic contact dermatitis (Bennassar et al., *Dermatology Online Journal*

15:14 (2009); Rietschel, R. L. Fisher's Contact Dermatitis. (Pmph Usa; 6 edition (Apr. 2, 2007)).

There remains a need for topical formulations containing UV filters/UV blockers for safe application to the skin.

It is therefore an object of the present invention to provide particles in topical formulations for use in sunscreens as well as therapeutic, prophylactic, diagnostic, nutraceutical and cosmetic applications.

It is a further object of the present invention to provide methods of making the particles and their topical formulations.

It is another object of the present invention to provide methods of using the particles and their topical formulations.

SUMMARY OF THE INVENTION

Core-shell particles, such as microparticles and nanoparticles, and methods of making and using thereof are described herein. The core is formed of or contains a hydrophobic material, preferably polymeric. The shell is formed of or contains a hyperbranched polymer (HP) with hydroxyl groups, such as a hyperbranched polyglycerol (HPG), hyperbranched peptides (HPP), hyperbranched oligonucleotides (HON), hyperbranched polysaccharides (HPS), and hyperbranched polyunsaturated or saturated fatty acids (HPF). The HP can be covalently bound to the one or more materials that form the core such that the hydrophilic HP is oriented towards the outside of the particles and the hydrophobic material oriented to form the core.

The HP coating can be modified to adjust the properties of the particles. For example, unmodified HP coatings impart stealth properties to the particles which resist non-specific protein absorption and are referred to as nonbioadhesive nanoparticles (NNPs). Alternatively, the hydroxyl groups on the HP coating can be chemically modified to form functional groups that react with functional groups on tissue or otherwise interact with tissue to adhere the particles to the tissue, cells, or extracellular materials, such as proteins. Such functional groups include, but are not limited to, aldehydes, amines, and O-substituted oximes. Particles with an HP coating chemically modified to form functional groups are referred to as bioadhesive nanoparticles (BNPs). The chemically modified HP coating of BNPs forms a bioadhesive corona of the particle surrounding the hydrophobic material forming the core.

Topical formulations containing these HP coated nanoparticles are useful for application to the skin of encapsulated therapeutic, prophylactic, cosmeceutical, or diagnostic agents. Nanoparticles with unusually strong bioadhesive properties do not diffuse into hair follicles and are useful as sunscreens, insect repellant, in cosmetic applications or for the delivery of cosmetic, therapeutic, prophylactic, diagnostic or nutraceutical agents.

The hydrophobic core of the NNPs and BNPs may include one or more active agents. The core may be varied in size. The core may be formed of two or more layers of hydrophobic material containing the agent, so that the release of the active agent is controlled. For example, the size of the core may be varied to vary the depth of penetration of the NNPs into the follicles following topical administration of a formulation containing the NNPs. The core may be formed for extended release of the active agent, so that the active agent is not released, or released within a defined time period such as 2, 4, 8, or 24 hours following application of the topical formulation containing the NNPs and/or BNPs. In other embodiments, the core may be formed of two or more layers of hydrophobic material, each layer containing one or more different agents, and each layer releasing the one or more different agents at specific times for controlled release.

Typically, the NNPs are non-adherent to biological tissues and display follicular penetrance, while BNPs are adherent to biological tissues and display no or minimal follicular penetrance. The HP coating can be partially chemically modified to provide a varying degree of adherence of the particles to biological tissues, cells, or extracellular materials, such as proteins.

In preferred embodiments, sunblock formulations are made by incorporation of chemical and/or non-chemical sunscreen agents into BNPs, such as oxybenzone, dioxybenzone, octinoxate, homosalate, octisalate, octocrylene, avobenzone, mexoryl SX, padimate O, p-aminobenzoic acid (PABA), phenylbenzimidazole sulfonic acid, cinoxate, menthyl anthranilate, sulisobenzone, parsol compounds, tinosorb compounds, and heliopan compounds, and non-chemical sunblock agents such as zinc oxide, titanium dioxide. The BNPs can also be used in topical formulations for artificial skin tanners. Pigment/melanin/melanin derivatives can be incorporated, optionally along with agents for protection against ultraviolet light exposure as well as for cosmetic uses, including by direct manual application to the skin and by spray applications.

In another preferred embodiment, formulations are prepared for treatment and/or prevention of aging and cellular/DNA damage, pre-malignant (actinic keratosis), and skin cancer. These formulations are made by incorporation of anti-oxidants, vitamins, minerals, polyphenols, retinoids, enzymes, growth factors and growth factor inhibitors, cytokines and cytokine inhibitors, and/or other anti-cancer and sunblock agents into BNPs. Examples of natural/herbal antioxidants include curcumin, lycopene, lutein, and alpha-lipoic acid (ALA). Examples of vitamins and their derivatives include ascorbic acid (vitamin C), vitamin A, vitamin B3, vitamin E, beta-carotene, and nicotinomide. Examples of minerals include selenium and zinc. Examples of useful polyphenols include soy-derived genistein. Other dietary agents/supplements include resveratrol, retinols and retinoids. Examples of useful enzymes include superoxide dismutase (SOD), catalase (CAT), glutathione peroxidase (GSHpx), glutathione reductase, nitric oxide synthases (NOS-1,-2,-3). Examples of useful anti-aging/skin cancer prevention compounds (alone or in combination with sunblock agents) include inhibitors of tumor promoting growth factors, such as inhibitors of epidermal growth factors, e.g. EDGF, KGF; and IGF, inhibitors of tumor-promoting cytokines, e.g. interleukin-22, GRO-1, and AREG, CYP1B1, direct and specific inhibitors of CYP1B1, general inhibitors of P450 enzymes, and inhibitors of the aryl hydrocarbon receptor (AHR), as well as CYP1A1 and its inducers, and other metabolizing agents that detoxify active mutagens/carcinogens.

Examples of anti-pathogen (anti-bacterial, anti-viral, anti-fungal) and microbiome altering formulations include topical formulations incorporating agents for the prevention and/or treatment of cutaneous bacterial infections, as well as the alteration of skin bacterial colonization and alterations to the normal/current state of skin flora. These may be useful for the treatment and/or prevention of impetigo, bacterial folliculitis, cellulitis (typically due to, but not limited to, *Staphylococcal* and *Streptococcal* ssp.), hot tub folliculitis (typically due to, but not limited to, *Pseudomonas* ssp.), pre- and post-procedure prevention of infections, by application to sites of skin for biopsy, surgery (including arthroscopic and laproscopic), or other invasive procedures that access via the skin. The formulations may be particularly applicable to the prevention and/or treatment of methicillin-resistant *Staphylococcus aureus* (MRSA) infections, as it relates to the incorporation of antibiotics generally, and specifically as it relates to the incorporation of agents that are not typically used in topical applications due to their toxicity, limited penetration into the skin, and/or inability to persist at the skin. Examples of antibacterial compounds that can be incorporated include vancomycin and other antibiotics used specifically to treat MRSA, triclosan, silver (ionic), benzoyl peroxide, other related agents, and bacterial nitric oxide synthase (NOS) inhibitors.

Anti-fungal agents, including nitric oxide (NO), and NO releasing solutions, can be incorporated into BNPs and NNPs for the prevention and/or treatment of cutaneous fungal infections, as well as the alteration of skin fungal colonization and alterations to the normal/current state of skin flora, such as tinea corporis, tinea pedis, tinea capitas, tinea barbae, toe nail fungal infections (tinea unguium), candidal infections, including intertrigo (e.g. inframammary, inguinal, gluteal), perleche/angular chelitis, vaginal moniliasis, balanitis, and *Pityrosporum* infections/overgrowth states (e.g. pityriasis versicolor, *pityrosporum* folliculitis).

Topical formulations incorporating anti-viral agents such as acyclovir, famcyclovir, and valacyclovir, into BNPs and NNPs can be used for the prevention and/or treatment of cutaneous viral infections/reactivation, including Herpes simplex virus (HSV) by application to lips, genitals and surrounding areas; Varicella zoster virus (VZV) by application to prior and/or suspected dermatomal eruptions, and Human papilloma virus (HPV)-related conditions (warts, including genital warts; HPV-related intraepithelial neoplasia/carcinoma, including oral, cervical, genital cancers) by application to prior and/or suspected lesions. Anti-viral agents can also be incorporated into BNPs for the prevention of systemic viral infections, including hepatitis B virus (HBV), hepatitis C virus (HCV), and human immunodeficiency virus (HIV).

Anti-inflammatory agents can be incorporated into BNPs and NNPs for the prevention and/or of treatment of inflammatory skin diseases, including atopic dermatitis, allergic contact dermatitis (e.g. poison ivy), psoriasis, dermatitis NOS, cutaneous lupus erythematosus, vitiligo, and alopecia areata. Exemplary anti-inflammatory agents include corticosteroids and non-steroidal anti-inflammatory drugs (NSAIDs) such as aspirin and ibuprofen, Jak and/or Stat inhibitors, and dapsone.

Anti-acne agents can be incorporated into BNPs and NNPs for prevention and/or of treatment of acne vulgaris, hydradenitis suppurative, folliculitis decalvans, and dissecting folliculitis. Exemplary agents include benzyol peroxide, retinoids, including tretinoin, and dapsone, and tumor necrosis factor-alpha (TNF-α) inhibitors and other anti-inflammatory agents.

In other embodiments, topical formulations include NNPs and BNPs for the stimulation of hair growth to treat conditions that cause alopecia, including androgenetic alopecia, alopecia areata, traction alopecia, scarring alopecia, and lichen planopilaris. Suitable agents for incorporation into NNPs and BNPs for the stimulation of hair growth include growth factors, such as fibroblast growth factors (FGFs), KFG (keratinocyte growth factors), EDGFs (epidermal derived growth factors), inhibitors of dihydrotestosterone (DHT) receptor, and other hormone and hormone receptors, anti-inflammatory agents, including TNF-α inhibitors, NSAIDs, Jak and/or Stat inhibitors, and NKG2D inhibitors. In addition, topical formulations may include BNPs for the temporary filling of hair defects ("bald spots" or "thinning hair") and for purposes of hair thickening by using BNPs with polymers that mimic hair appearance and texture, alone or in combination with hair conditioners, dyes, and other hair products. In other embodiments, topical formulations may contain NNPs and/or BNPs targeted to the hair follicles and pores and sweat glands for hyperhydrosis control, as antiperspirants, and/or deodorants.

Structural or enzymatic proteins can be incorporated into BNPs and NNPs for the treatment and/or prevention of cutaneous diseases, such as filaggrin for atopic dermatitis or ichthyosis vulgaris, transglutaminase for autosomal-recessive congenital ichthyosis (ARCI), collagen VII for dystrophic epidermolysis bullosa (DEB), keratin 5 and/or 14 for epidermolysis bullosa simplex (EBS), and keratin 1 and/or 10 for bullous congenital ichthyosiform erythroderma (BCIE).

Topical formulations for stimulation of wound healing can incorporate agents such as growth factors, collagen, antibodies, extracellular matrix materials, fibrinogen and other products for the stimulation of wound healing, including that induced by trauma, surgical, diabetic, vascular occlusive, and/or chemical or thermal burn) via the stimulation of vascular elements, collagen production, and/or keratinocyte migration and proliferation. These can be administered alone or in combination with the anti-infective (antibacterial, antiviral or antifungal) formulations.

The BNPs and NNPs can be used in cosmetic products by incorporation of pigments, dyes, minerals, latex, silicon, and other ingredients, optionally further including protection against ultraviolet light exposure. These can be directly applied to the skin as a spray, liquid or foundation, concealer, eye liner, eye shadow, mascara, lip coloring/glossing. These are especially useful for treatment of fine and deep lines, grooves, and rhytides. Hair coloring dyes, holding products and hair thickening agents, such as dyes, pigment, minerals, adhesives, may also be incorporated into BNPs and NNPs, which can be applied directly to the hair or by spray or foam applications. The BNPs incorporating pigment can also be used in ink for temporary or permanent tattoos when applied to the skin or to hair. In other embodiments, BNPs or NNPs may be used as fragrance additives in perfumes or colognes. For example, topical formulations containing BNPs or NNPs may be used as fragrances, perfumes, colognes, after-shave products by incorporation of fragrances into BNPs or NNPs. These topical formulations may prevent penetration of fragrances into the skin thereby decreasing the risk of irritancy and allergic reaction.

In some embodiments, the bioadhesive corona of the BNPs may allow the BNPs to fill cavities, or be stacked in layers. For example, topical formulations containing BNPs may be used to fill in wrinkles, or stacked as hair-like polymers to thicken hair and cover alopecic areas. In these embodiments, the BNPs are self-adhering or self-binding.

In another embodiment the BNPs incorporate insect/arthropod/arachnid repellents/pesticides for the prevention of bites and stings (e.g. mosquitos, ticks, bedbugs, flies, lice), as well as vector transmission of percutaneously introduced diseases such as malaria, Lyme disease, leismaniasis, and Chagas disease. Exemplary insect repellents include DEET (N,N-diethyl-m-toluamide), natural/essential oil insect repellents such as citronella oil, Neem oil, birch tar, and bog myrtle, and permethrin. These formulations may be effective with lower concentrations of agent, or decreased toxicity, due to the BNP formulation. The formulations, especially if applied to the hair, are particularly useful in the treatment/prevention of lice outbreaks.

NNPs and BNPs can also be formulated with chemotherapeutic agents and other pharmacological agents for the treatment of cancer. Therapeutically effective amounts of the disclosed particles used in the treatment of cancer will generally kill tumor cells or inhibit proliferation or metastasis of the tumor cells. The cancer can be a skin cancer. In particular embodiments the strategy is utilized to target treat a cutaneous tumor type, such as malignant (melanoma, squamous cell carcinoma, basal cell carcinoma, merkel cell carcinoma, dermatofibroma sarcoma protuberans, cutaneous T cell lymphoma, cutaneous B cell lymphoma) premalignant (actinic keratoses, dysplastic nevi), photodamaged or aging skin changes (lentigos, rhytides), and benign neoplasms (dermatofibromas, lipomas, seborrheic keratoses). Anti-cancer agents/active pharmacologic ingredients APIs incorporated into BNPs and NNPs may be (1) directly toxic to tumor cells, as in chemotherapeutic agents generally, (2) immune modifying, as in TLR agonists like imiquimod, and/or (3) inhibitors (cytokines, toxins, or other APIs) of tumor associated macrophages (TAMs) that are known to decrease anti-tumor immunity. In particularly preferred embodiments, BNPs are loaded with an anti-cancer agent and show improved cancer treatment compared to NNPs loaded with the drug.

BRIEF DESCRIPTION OF THE DRAWINGS

FIG. 7A is a bar graph showing epidermal thickness (microns) after receiving different topical interventions. FIG. 7B is a bar graph showing normalized percent area of keratin within the dorsal skin after receiving different interventions. The interventions were: A) Normal skin, B) Sunscreen, C) PO/PLA-HPG$_{ALD}$ NPs, D) blank PLA-HPG$_{ALD}$ NPs, and E) No treatment.

FIG. 8 is a bar graph showing fluorescence (arbitrary units) of cyclopyrimidine dimers (CPD) on skin that received different topical interventions. Data are shown as mean±SD (n=3), **p<0.01 (student t-test). PO/BNP—bioadnesive nanoparticles (PLA-HPG$_{ALD}$ NPs) encapsulating PO, PO—padamate O.

FIG. 10A is a diagram of sunscreen formulations applied onto the skin. FIG. 10B is a diagram of the skin after application: regular sunscreen penetrates into the skin whereas the PLA-HPG$_{ALD}$ NP (BNPs) formulation remains on the stratum corneum. FIG. 10C is a diagram of the skin after sunlight exposure: UV filters produce deleterious ROS, however, PLA-HPG$_{ALD}$ NPs (BNPs) do not penetrate into the skin and prevent ROS mediated toxicity by confining these toxic products within the particle. BNP—bioadhesive nanoparticles (PLA-HPG$_{ALD}$ NPs), UV—ultraviolet.

DETAILED DESCRIPTION OF THE INVENTION

I. Definitions

Figure 1A:
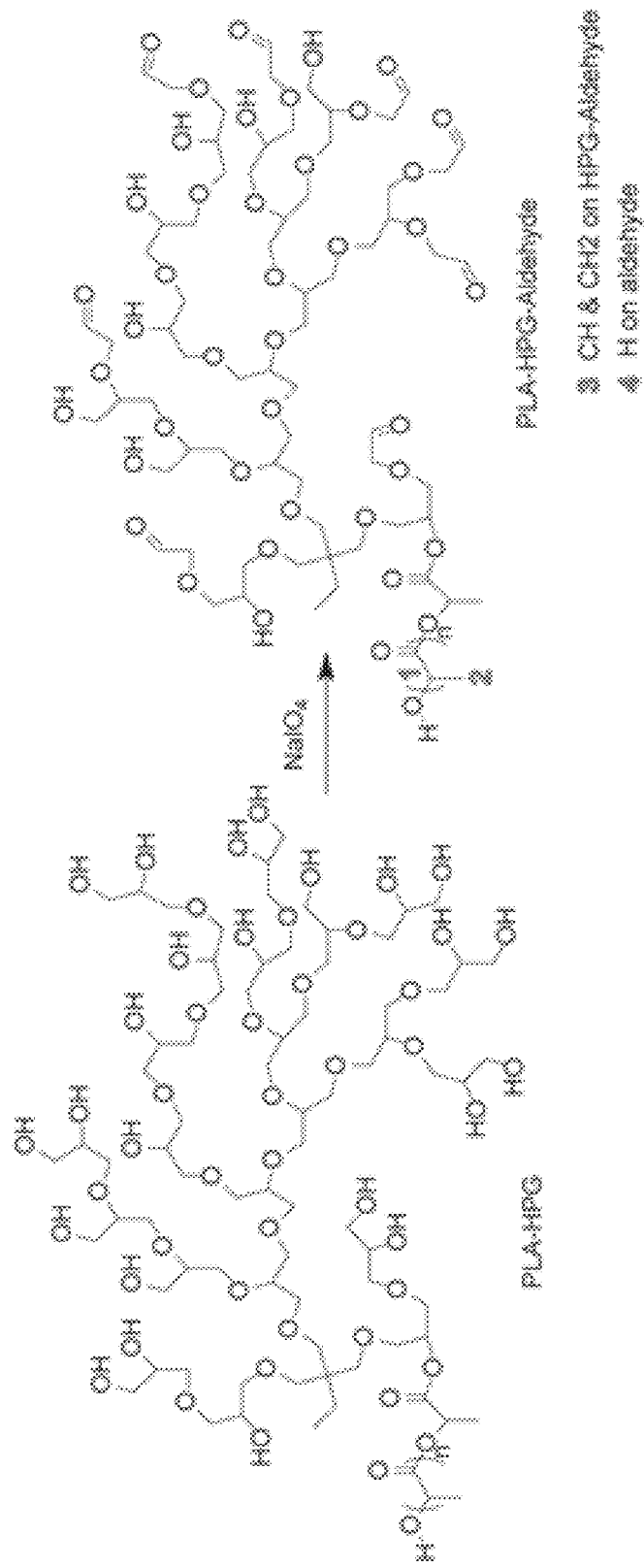
FIG. 1A is a schematic of bioadhesive PLA-HPG$_{ALD}$.

"Sunblock" or "sunscreen", as used herein, are used interchangeably to refer to one or more agents that block or filter ultraviolet light. Sunblock/sunscreen agents provide protection against UVA, UVB, or both UVA and UVB light "Sunblock formulation" or "Sunscreen formulation" are formulations containing one or more sunblock/sunscreen agent(s).

"Effective amount" or "therapeutically effective amount", as used herein, refers to an amount of agent effective to alleviate, delay onset of, or prevent one or more symptoms of a disease or disorder, to reduce penetration of UVB and UVA light into the skin, or to reduce the number of insect/arthropod/arachnoid bites, to improve hair growth or appearance, or to provide a desired look, color, complexion, or fragrance to an area of the skin, as described herein, using criteria known and used by those skilled in the art.

The terms "treating" or "preventing", as used herein, can include preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

"Topical administration", as used herein, means the non-invasive administration to the skin, orifices, or mucosa. Topical administrations can be administered locally, i.e. they are capable of providing a local effect in the region of application without systemic exposure. Topical formulations can provide systemic effect via adsorption into the blood stream of the individual. Topical administration can include, but is not limited to, cutaneous and transdermal administration, buccal administration, intranasal administration, intravaginal administration, intravesical administration, ophthalmic administration, and rectal administration.

The terms "bioactive agent" and "active agent", as used interchangeably herein, include, without limitation, physiologically or pharmacologically active substances that act locally or systemically in the body. A bioactive agent is a substance used for the treatment (e.g., therapeutic agent), prevention (e.g., prophylactic agent), diagnosis (e.g., diagnostic agent), cure or mitigation of disease or illness, a substance which affects the structure or function of the body, or pro-drugs, which become biologically active or more active after they have been placed in a predetermined physiological environment.

"Biocompatible" and "biologically compatible", as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "pharmaceutically acceptable", as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration. A "pharmaceutically acceptable carrier", as used herein, refers to all components of a pharmaceutical formulation which facilitate the delivery of the composition in vivo. Pharmaceutically acceptable carriers include, but are not limited to, diluents, preservatives, binders, lubricants, disintegrators, swelling agents, fillers, stabilizers, and combinations thereof.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

The term "small molecule", as used herein, generally refers to an organic molecule that is less than about 2000 g/mol in molecular weight, less than about 1500 g/mol, less than about 1000 g/mol, less than about 800 g/mol, or less than about 500 g/mol. Small molecules are non-polymeric and/or non-oligomeric.

The term "copolymer" as used herein, generally refers to a single polymeric material that is comprised of two or more different monomers. The copolymer can be of any form, such as random, block, graft, etc. The copolymers can have any end-group, including capped or acid end groups.

"Hydrophilic," as used herein, refers to the property of having affinity for water. For example, hydrophilic polymers (or hydrophilic polymer segments) are polymers (or polymer segments) which are primarily soluble in aqueous solutions and/or have a tendency to absorb water. In general, the more hydrophilic a polymer is, the more that polymer tends to dissolve in, mix with, or be wetted by water.

"Hydrophobic," as used herein, refers to the property of lacking affinity for, or even repelling water. For example, the more hydrophobic a polymer (or polymer segment), the more that polymer (or polymer segment) tends to not dissolve in, not mix with, or not be wetted by water.

Hydrophilicity and hydrophobicity can be spoken of in relative terms, such as, but not limited to, a spectrum of hydrophilicity/hydrophobicity within a group of polymers or polymer segments. In some embodiments wherein two or more polymers are being discussed, the term "hydrophobic polymer" can be defined based on the polymer's relative hydrophobicity when compared to another, more hydrophilic polymer.

The term "lipophilic", as used herein, refers to compounds having an affinity for lipids.

The term "amphiphilic", as used herein, refers to a molecule combining hydrophilic and lipophilic (hydrophobic) properties.

"Nanoparticle", as used herein, generally refers to a particle having a diameter, such as an average diameter, from about 10 nm up to but not including about 1 micron, preferably from 100 nm to about 1 micron. The particles can have any shape. Nanoparticles having a spherical shape are generally referred to as "nanospheres".

"Microparticle", as used herein, generally refers to a particle having a diameter, such as an average diameter, from about 1 micron to about 100 microns, preferably from about 1 to about 50 microns, more preferably from about 1 to about 30 microns, most preferably from about 1 micron to about 10 microns. The microparticles can have any shape. Microparticles having a spherical shape are generally referred to as "microspheres".

"Mean particle size" as used herein, generally refers to the statistical mean particle size (diameter) of the particles in a population of particles. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Stealth", as used herein, refers to the property of nanoparticles. These nanoparticles are not cleared by the mononuclear phagocyte system (MPS) due to the presence of the hydroxyl groups. The stealth particles resist non-specific protein absorption.

"Monodisperse" and "homogeneous size distribution", are used interchangeably herein and describe a population of nanoparticles or microparticles where all of the particles are the same or nearly the same size. As used herein, a monodisperse distribution refers to particle distributions in which 90% or more of the distribution lies within 15% of the median particle size, more preferably within 10% of the median particle size, most preferably within 5% of the median particle size.

"Branch point", as used herein, refers to a portion of a polymer-drug conjugate that serves to connect one or more hydrophilic polymer segments to one or more hydrophobic polymer segments.

The term "targeting moiety", as used herein, refers to a moiety that binds to or localizes to a specific locale. The moiety may be, for example, a protein, nucleic acid, nucleic acid analog, carbohydrate, or small molecule. The locale may be a tissue, a particular cell type, or a subcellular compartment. The targeting moiety or a sufficient plurality of targeting moieties may be used to direct the localization of a particle or an active entity. The active entity may be useful for therapeutic, prophylactic, or diagnostic purposes.

The term "reactive coupling group", as used herein, refers to any chemical functional group capable of reacting with a second functional group to form a covalent bond. The selection of reactive coupling groups is within the ability of the skilled artisan. Examples of reactive coupling groups can include primary amines (—NH$_2$) and amine-reactive linking groups such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. Most of these conjugate to amines by either acylation or alkylation. Examples of reactive coupling groups can include aldehydes (—COH) and aldehyde reactive linking groups such as hydrazides, alkoxyamines, and primary amines. Examples of reactive coupling groups can include thiol groups (—SH) and sulfhydryl reactive groups such as maleimides, haloacetyls, and pyridyl disulfides. Examples of reactive coupling groups can include photoreactive coupling groups such as aryl azides or diazirines. The coupling reaction may include the use of a catalyst, heat, pH buffers, light, or a combination thereof.

The term "protective group", as used herein, refers to a functional group that can be added to and/or substituted for another desired functional group to protect the desired functional group from certain reaction conditions and selectively removed and/or replaced to deprotect or expose the desired functional group. Protective groups are known to the skilled artisan. Suitable protective groups may include those described in Greene, T. W. and Wuts, P. G. M., Protective Groups in Organic Synthesis, (1991). Acid sensitive protective groups include dimethoxytrityl (DMT), tert-butylcarbamate (tBoc) and trifluoroacetyl (tFA). Base sensitive protective groups include 9-fluorenylmethoxycarbonyl (Fmoc), isobutyrl (iBu), benzoyl (Bz) and phenoxyacetyl (pac). Other protective groups include acetamidomethyl, acetyl, tert-amyloxycarbonyl, benzyl, benzyloxycarbonyl, 2-(4-biphenylyl)-2-propyloxycarbonyl, 2-bromobenzyloxycarbonyl, tert-butyl, tert-butyloxycarbonyl, 1-carbobenzoxamido-2,2.2-trifluoroethyl, 2,6-dichlorobenzyl, 2-(3,5-dimethoxyphenyl)-2-propyloxycarbonyl, 2,4-dinitrophenyl, dithiasuccinyl, formyl, 4-methoxybenzenesulfonyl, 4-methoxybenzyl, 4-methylbenzyl, o-nitrophenylsulfenyl, 2-phenyl-2-propyloxycarbonyl, α-2,4,5-tetramethylbenzyloxycarbonyl, p-toluenesulfonyl, xanthenyl, benzyl ester, N-hydroxysuccinimide ester, p-nitrobenzyl ester, p-nitrophenyl ester, phenyl ester, p-nitrocarbonate, p-nitrobenzylcarbonate, trimethylsilyl and pentachlorophenyl ester.

"About" is intended to describe values either above or below the stated value in a range of approx. +/−10%. The ranges are intended to be made clear by context, and no further limitation is implied. The use of any and all examples, or exemplary language (e.g., "such as") provided herein, is intended merely to better illuminate the description and does not pose a limitation on the scope of the description unless otherwise claimed.

II. Core-shell Microparticles and Nanoparticles

A. Core

The core of the particles is formed of or contains one or more hydrophobic materials, typically polymers (e.g., homopolymer, copolymer, terpolymer, etc.) or other hydrophobic molecules such as alkanes, drugs, hydrophobic peptides, PNA, and nucleic acid molecules. The material may be biodegradable or non-biodegradable. In some embodiments, the one or more materials are one or more biodegradable polymers.

In general, synthetic polymers are preferred, although natural polymers may be used and have equivalent or even better properties, especially some of the natural biopolymers which degrade by hydrolysis, such as some of the polyhydroxyalkanoates. Representative synthetic polymers are: poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulfate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), copolymers and blends thereof. Examples of preferred natural polymers include proteins such as albumin, collagen, gelatin and prolamines, for example, zein, and polysaccharides such as alginate, cellulose derivatives and polyhydroxyalkanoates, for example, polyhydroxybutyrate. As used herein, "derivatives" include polymers having substitutions, additions of chemical groups and other modifications routinely made by those skilled in the art.

Examples of preferred non-biodegradable polymers include ethylene vinyl acetate, poly(meth)acrylic acid, polyamides, copolymers and mixtures thereof.

In certain embodiments, the hydrophobic polymer is an aliphatic polyester. In preferred embodiments, the hydrophobic polymer is a polyhydroxyester such as poly(lactic acid), poly(glycolic acid), or poly(lactic acid-co-glycolic acid). The particles are designed to release molecules to be encapsulated or attached over a period of days to weeks. Factors that affect the duration of release include pH of the surrounding medium (higher rate of release at pH 5 and below due to acid catalyzed hydrolysis of PLGA) and polymer composition. Aliphatic polyesters differ in hydrophobicity and that in turn affects the degradation rate. The hydrophobic poly (lactic acid) (PLA), more hydrophilic poly (glycolic acid) PGA and their copolymers, poly (lactide-co-glycolide) (PLGA) have different release rates. The degradation rate of these polymers, and often the corresponding drug release rate, can vary from days (PGA) to months (PLA) and is easily manipulated by varying the ratio of PLA to PGA. The core can be formed of copolymers including amphiphilic copolymers such as PLGA-PEG or PLURONICS (block copolymers of polyethylene oxide-polypropylene glycol) but this may decrease the benefit of the polyglycerol molecules discussed below.

Other materials may also be incorporated including lipids, fatty acids, and phospholipids. These may be dispersed in or on the particles, or interspersed with the polyglycerol coatings discussed below.

In particular embodiments, NPs core is formulated of poly-lactic acid (PLA); poly-D-L-glycolide (PLG); poly-D-L-lactide-co-glycolide (PLGA); and poly-cyanoacrylate (PCA); poly-ε-caprolactone (PCL); poly-alkyl-cyano-acrylates (PAC); chitosan (a modified natural carbohydrate polymer prepared by the partial N-deacetylation of the crustacean-derived natural biopolymer chitin); gelatin (a polyampholyte consisting of both cationic and anionic groups along with a hydrophilic group); or combinations thereof.

1. Core Size

The core may vary in size or the core may be formed of two or more layers of hydrophobic material containing the agent, so that the site, duration and manner of release of the active agents are controlled. For example, the varying size of the core may control the depth of penetration of the NNPs into the follicle following topical administration of a formulation containing the NNPs.

2. Core for Controlled Release of Agents

In other embodiments, the core may be formed for extended release of the active agent, so that the active agent is not released, or released within 2, 4, 8, or 24 hours following application of the topical formulation containing the NNPs and/or BNPs. In other embodiments, the core may be formed of two or more layers of hydrophobic material, each layer containing one or more different agents, and each layer releasing the one or more different agents at specific times to provide for controlled release of the agent.

As used herein, "controlled release" refers to a release profile of an agent for which the agent release characteristics of time course and/or location are chosen to accomplish therapeutic or convenience objectives not offered by conventional topical formulations. Delayed release, extended release, and pulsatile release and their combinations are types of controlled release. In preferred formulations, nanoparticle core includes a combination of extended release components, rapid release components, immediate release components, and delayed release components to provide the desired release profile and/or pharmacokinetic parameters. The formulations can have nanoparticles with cores of multiphasic release profile. As used herein, a "multiphasic release profile" refers to an agent release profile having multiple distinct phases or stages, for example, a "biphasic release profile" refers to a release profile having two distinct phases or stages and a "triphasic release profile" refers to a release profile having three distinct phases or stages. Both are examples of multiphasic release.

For example, an agent can be formulated into nanoparticle or microparticle core with an extended release polymer or matrix. The core can be coated with one or more immediate release and/or rapid release dosing layers containing additional agent providing release of the agent at certain times. The rapid release dosing layers can optionally have a delayed release or be coated with a delayed release polymer coating.

The term "immediate release" (IR) refers to release of an active agent to an environment over a period of seconds to up to about 30 minutes once release has begun and release begins within a second to no more than about 10 minutes after exposure to an aqueous environment.

"Rapid release" as used herein refers to release of an active agent to an environment over a period of seconds to no more than about 60 minutes once release has begun and release can begin within a few seconds or minutes after exposure to an aqueous environment or after completion of a delay period (lag time) after exposure to an aqueous environment.

a. Extended Release

Cores of NNPs and BNPs for extended release of the agent are generally prepared as diffusion or osmotic systems, which are known in the art. A diffusion system typically consists of one of two types of devices, a reservoir or a matrix, and is well known and described in the art. The matrix devices are generally prepared by compressing the agent with a slowly dissolving polymer carrier into the core. The three major types of materials used in the preparation of matrix devices are hydrodphobic polymers, hydrophilic polymers, and fatty compounds. Polymeric matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such ashydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain embodiments, the polymer material is a pharmaceutically acceptable acrylic polymer, including, but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers. In certain embodiments, the acrylic polymer is comprised of one or more ammonio methacrylate copolymers. Ammonio methacrylate copolymers are well known in the art, as fully polymerized copolymers of acrylic and methacrylic acid esters with a low content of quaternary ammonium groups.

In one embodiment, the acrylic polymer is an acrylic resin lacquer such as that which is commercially available from Rohm Pharma under the tradename EUDRAGIT®. In other embodiments, the acrylic polymer may be a mixture of two acrylic resin lacquers commercially available from Rohm Pharma under the tradenames EUDRAGIT® RL30D and EUDRAGIT® RS30D, respectively. EUDRAGIT® RL30D and EUDRAGIT® RS30D are copolymers of acrylic and methacrylic esters with a low content of quaternary ammonium groups, the molar ratio of ammonium groups to the remaining neutral (meth)acrylic esters being 1:20 in EUDRAGIT® RL30D and 1:40 in EUDRAGIT® RS30D. The mean molecular weight is about 150,000. EUDRAGIT® S-100 and EUDRAGIT® L-100 are also preferred. The code designations RL (high permeability) and RS (low permeability) refer to the permeability properties of these agents. EUDRAGIT® RL/RS mixtures are insoluble in water and in digestive fluids. However, multiparticulate systems formed to include the same are swellable and permeable in aqueous solutions and digestive fluids.

The polymers such as EUDRAGIT® RL/RS may be mixed together in any desired ratio in order to ultimately obtain an extended-release core having a desirable dissolution profile. Desirable sustained-release multiparticulate systems may be obtained, for instance, from 100% EUDRAGIT®, 50% EUDRAGIT® RL and 50% EUDRAGIT® RS, and 10% EUDRAGIT® RL and 90%: EUDRAGIT® 90% RS. One skilled in the art will recognize that other acrylic polymers may also be used, such as, for example, EUDRAGIT® L.

Alternatively, extended release components can be prepared using osmotic systems or by applying a semi-permeable coating to the core. In the latter case, the desired agent release profile can be achieved by combining low permeable and high permeable coating materials in suitable proportion.

In another embodiment, the agent is dispersed in a matrix material which gels or emulsifies upon contact with an aqueous medium, such as physiological fluids. In the case of gels, the matrix swells entrapping the active agents, which are released slowly over time by diffusion and/or degradation of the matrix material.

b. Delayed Release Components

Delayed release formulations can be created by coating agents and/or cores with a polymer film which is insoluble in the acidic environments and soluble in the neutral environments. Such pH dependent polymers include, but is not limited to, methyl acrylate-methacrylic acid copolymers, cellulose acetate succinate, hydroxy propyl methyl cellulose phthalate, hydroxy propyl methyl cellulose acetate succinate (hypromellose acetate' succinate), polyvinyl acetate phthalate (PVAP), methyl methacrylate-methacrylic acid copolymers, sodium alginate and stearic acid.

B. Shell or Corona

The particles typically include a shell, corona or coating of or containing hyperbranched polymers (HP). Suitable polymers for forming the shell or corona include biodegradable polymeric molecules, such as polyglycerols, polypeptides, oligonucleotides, polysaccharides, and fatty acids. Hyperbranched polyglycerol (HPG) is an exemplary hyperbranched polymer.

1. HPG

In preferred embodiments, the polymer is hyperbranched polyglycerol (HPG). HPG is a highly branched polyol containing a polyether scaffold. Hyperbranched polyglycerol can be prepared using techniques known in the art. It can be formed from controlled etherification of glycerol via cationic or anionic ring opening multibranching polymerization of glycidol. For example, an initiator having multiple reactive sites is reacted with glycidol in the presence of a base to form hyperbranched polyglycerol (HPG). Suitable initiators include, but are not limited to, polyols, e.g., triols, tetraols, pentaols, or greater and polyamines, e.g., triamines, tetraamines, pentaamines, etc. In one embodiment, the initiator is 1,1,1-trihydroxymethyl propane (THP).

A formula for hyperbranched polyglycerol as described in EP 2754684 is

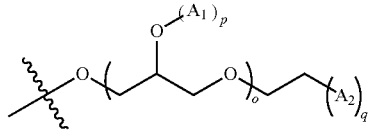

Formula I wherein o, p and q are independently integers from 1-100, wherein $A_1$ and $A_2$ are independently

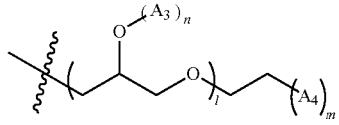

Formula II wherein l, m and n are independently integers from 1-100. wherein $A_3$ and $A_4$ are defined as $A_1$ and $A_2$, with the proviso that $A_3$ and $A_4$ are hydrogen, n and m are each 1 for terminal residues.

The surface properties of the HPG can be adjusted based on the chemistry of vicinal diols. For example, the surface properties can be tuned to provide stealth particles, i.e., particles that are not cleared by the MPS due to the presence of the hydroxyl groups; adhesive (sticky) particles, i.e., particles that adhere to the surface of tissues, for example, due to the presence of one or more reactive functional groups, such as aldehydes, amines, oxime, or O-substituted oxime that can be prepared from the vicinal hydroxyl moieties; or targeting by the introduction of one or more targeting moieties which can be conjugated directly or indirectly to the vicinal hydroxyl moieties. Indirectly refers to transformation of the hydroxy groups to reactive functional groups that can react with functional groups on molecules to be attached to the surface, such as active agents and/or targeting moieties, etc. A schematic of this tunability is shown in FIG. 1A showing bioadhesive polymer.

The hyperbranched nature of the polyglycerol allows for a much higher density of hydroxyl groups, reactive functional groups, and/or targeting moieties than obtained with linear polyethylene glycol. For example, the particles can have a density of surface functionality (e.g., hydroxyl groups, reactive functional groups, and/or targeting moieties) of at least about 1, 2, 3, 4, 5, 6, 7, or 8 groups/nm$^2$.

The molecular weight of the HPG can vary. For example, in those embodiments wherein the HPG is covalently attached to the materials or polymers that form the core, the molecular weight can vary depending on the molecular weight and/or hydrophobicity of the core materials. The molecular weight of the HPG is generally from about 1,000 to about 1,000,000 Daltons, from about 1,000 to about 500,000 Daltons, from about 1,000 to about 250,000 Daltons, or from about 1,000 to about 100,000 Daltons. In those embodiments wherein the HPG is covalently bound to the core materials, the weight percent of HPG of the copolymer is from about 1% to about 50%, such as about 1, 2, 3, 4, 5, 10, 15, 20, 25, 30, 35, 40, 45 or 50%.

In some embodiments, the HPG is covalently coupled to a hydrophobic material or a more hydrophobic material, such as a polymer. Upon self-assembly, particles are formed containing a core containing the hydrophobic material and a shell or coating of HPG. HPG coupled to the polymer PLA is shown below:

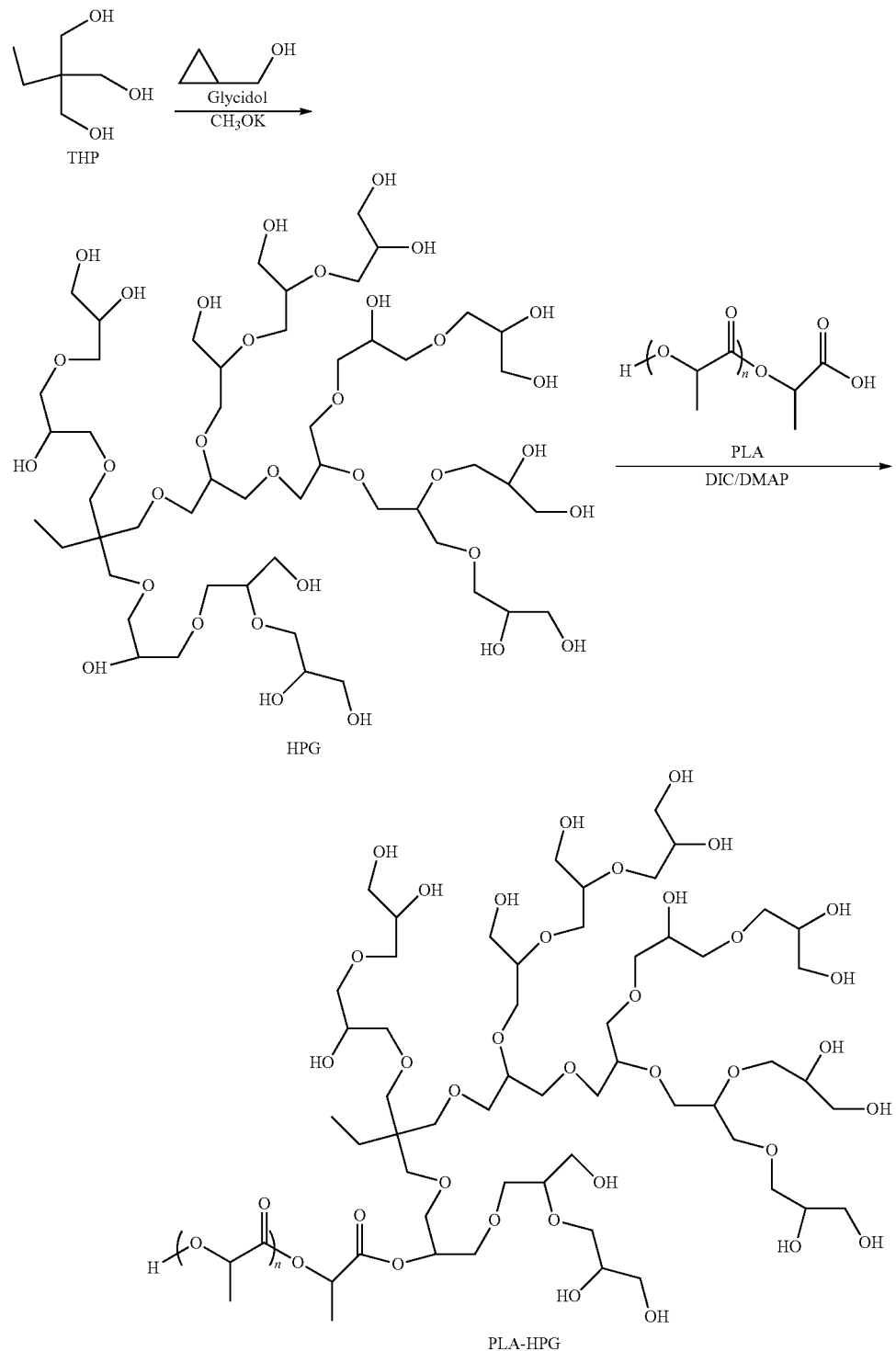

2. Other Polymers for Forming A Shell, Corona or Coating.

NPs with bioadhesive coronas (i.e., BNPs) are not limited to hyperbranched polyglycerols and their associated aldehydes, but may include other biodegradable polymers and molecules such as peptides formed of amino acids and, oligonucleotides formed of nucleic acids, polysaccharides and fatty acids. These polymers or small molecules, when converted to an aldehyde-terminated form, are adhesive.

Suitable materials for forming bioadhesive functional groups are materials that have aldehydes or the potential to form aldehydes following chemical modification (e.g. sodium periodate ($NaIO_4$) treatment). These include polymers of saccharides such as dextran, cellulose, and other starches, polymers of or containing serine amino acids or materials with vicinal diol or serine structure (amine and hydroxyl on neighboring carbons), materials with hydroxyl groups, since the hydroxyl groups can be oxidized to aldehydes by catalysts such as Collins reagent, or any polymeric molecule, such as a dendrimer that may be attached with molecules containing aldehydes or has groups may be converted to aldehydes (Gao and Yan, *Prog. Polym. Sci.* 29:183-275 (2004)).

Below are the vicinal diols (most sugars have vicinal diols) and serine structures, which can be oxidized to aldehydes by $NaIO_4$ treatment.

Vicinal diols    Part of serine amino acid

Aldehyde containing molecules or particles are reactive with film formers containing amine or amine derivatives to form a film on the skin.

C. Molecules to be Encapsulated or Attached to the Surface of the Particles

The particles may contain one or more types of molecules encapsulated within and/or attached to the surface of the particles. The molecules can be covalently or non-covalently associated with the particles.

In preferred embodiments, the molecules are pigments or particles blocking or filtering ultraviolet ("UV") radiation.

In some embodiments, the molecules are targeting moieties which are covalently associated with the particles. In particular embodiments, the targeting moieties are covalently bound to the HPG coating via the hydroxy groups on HPG. The targeting moieties can be bound directly to HPG or via a coupling agent. In other embodiments, the particles have encapsulated therein one or more therapeutic agents, diagnostic agents, prophylactic agents, and/or nutraceuticals. In some embodiments, the particles contain both targeting agents which are covalently or non-covalently associated with the particles and one or more therapeutic agents, diagnostic agents, prophylactic agents, and/or nutraceuticals which are covalently or non-covalently associated with the particles.

Molecules can be bound to the hydroxy groups on HP before or after particle formation. Representative methodologies for conjugated molecules to the hydroxy groups on HPG are described below.

One useful protocol involves the "activation" of hydroxyl groups with carbonyldiimidazole (CDI) in aprotic solvents such as DMSO, acetone, or THF. CDI forms an imidazolyl carbamate complex with the hydroxyl group which may be displaced by binding the free amino group of a ligand such as a protein. The reaction is an N-nucleophilic substitution and results in a stable N-alkylcarbamate linkage of the ligand to the polymer. The "coupling" of the ligand to the "activated" polymer matrix is maximal in the pH range of 9-10 and normally requires at least 24 hrs. The resulting ligand-polymer complex is stable and resists hydrolysis for extended periods of time.

Another coupling method involves the use of 1-ethyl-3-(3-dimethylaminopropyl) carbodiimide (EDAC) or "water-soluble CDI" in conjunction with N-hydroxylsulfosuccinimide (sulfo NHS) to couple the exposed carboxylic groups of polymers to the free amino groups of ligands in a totally aqueous environment at the physiological pH of 7.0. Briefly, EDAC and sulfo-NHS form an activated ester with the carboxylic acid groups of the polymer which react with the amine end of a ligand to form a peptide bond. The resulting peptide bond is resistant to hydrolysis. The use of sulfo-NHS in the reaction increases the efficiency of the EDAC coupling by a factor of ten-fold and provides for exceptionally gentle conditions that ensure the viability of the ligand-polymer complex.

By using either of these protocols it is possible to "activate" almost all polymers containing either hydroxyl or carboxyl groups in a suitable solvent system that will not dissolve the polymer matrix.

A useful coupling procedure for attaching ligands with free hydroxyl and carboxyl groups to polymers involves the use of the cross-linking agent, divinylsulfone. This method would be useful for attaching sugars or other hydroxylic compounds with bioadhesive properties to hydroxylic matrices. Briefly, the activation involves the reaction of divinylsulfone to the hydroxyl groups of the polymer, forming the vinylsulfonyl ethyl ether of the polymer. The vinyl groups will couple to alcohols, phenols and even amines. Activation and coupling take place at pH 11. The linkage is stable in the pH range from 1-8.

Alternatively, the hydroxyl groups can be converted to reactive functional group that can react with a reactive functional group on the molecule to be attached. For example, the hydroxyl groups on HPG can be converted to aldehydes, amines, or O-substituted oximes which can react with reactive functional groups on molecules to be attached. Such transformations can be done before or after particle formation.

Any suitable coupling method known to those skilled in the art for the coupling of ligands and polymers with double bonds, including the use of UV crosslinking, may be used for attachment of molecules to the polymer.

Coupling is preferably by covalent binding but it may also be indirect, for example, through a linker bound to the polymer or through an interaction between two molecules such as streptavidin and biotin. It may also be by electrostatic attraction by dip-coating.

The most efficient reaction between —OH and —COOH is to use coupling reagents: DCC/DMAP and DIC/DMAP or activate the —COOH to —COCl and then react with —OH in the presence of pyridine.

The coupling methods can be done before or after particle formation.

The functionalization of polymer-HP can be obtained by coupling hydroxyl groups of the HP with a carboxylic group on a ligand. For example, an HP polymer, such as PLA-HPG polymer can be functionalized with a molecule, containing a carboxylic group. PLA-HPG can be added to the molecule and dissolved in a solvent such as anhydrous DMF. The solution can be dried with a molecular sieve with DIC and DMAP added to the solution. To purify the polymer, the solution can be added into cold diethyl ether to precipitate the polymer. The polymer precipitate can be collected and dissolved in a solvent such as DCM/TFA mixture in a ratio of DCM:TFA=2:1, and the reaction shaken at room temperature. The resulting solution can be added into cold another solvent such as diethyl ether and the polymer collected by centrifugation. The polymer can be further purified by redissolving in a solvent such as DCM and precipitating in another solvent such as diethyl ether. To confirm conjugation of the ligand to PLA-HPG, the polymers can be dissolved in DMSO-d6 and analyzed by $^1$H NMR. The PLA-HPG-ligand polymer can then be used to form PLA-HPG-ligand nanoparticles using, for example, an emulsion solvent evaporation technique.

The particles can be first prepared using, for example, an emulsion solvent evaporation technique. They can then be rendered "sticky" by converting the alcohol or hydroxyl groups of the HPG into aldehydes using $NaIO_4$. Following this treatment, the $NaIO_4$ can be quenched using $Na_2SO_3$ and the particles can be incubated with ligand to induce a Schiff base reaction between an amino-oxy group on the ligand (e.g., N-terminus of a peptide) and the aldehyde groups. After incubation, the unreacted ligand is washed by centrifugation, and the remaining reactive aldehyde groups on the HPG can be blocked by hydroxyl amine ($HONH_2$).

The hyperbranched polyglycerol (HPG) and aldehyde conversion can enhance bioadhesive properties of core polymer, including binding of bioadhesive coating directly to agent/polymer of interest (e.g. minerals, pigments, antibiotic agents, latex, silicon) and to biodegradable NPs more generally.

In some embodiments, formulations include only BNPs, only NNPs, or a combination of BNPs and NNPs.

1. Ultraviolet Light Filters and Pigments

Ultraviolet light filters (such as zinc oxide (ZnO), titanium dioxide (TiO2), avobenzone, tinosorb S, mexoryl SX, mexoryl XL, helioplex, octinoxate, octocrylene, oxybenzone, octisalate, homosalate, uvinul T 150, cinoxate, aminobenzoic acid, padimate O, ensulizole, dioxybenzone, meradimate, sulisobenzone, trolamine salicylate, enzacamene, bisdisulizole disodium, uvinul A Plus, uvasorb HEB, parsol SLX, amiloxate), antibiotics, antiseptics, antifungals, and anesthetic compounds (such as lidocaine, benzocaine, chloroprocaine, cyclomethycaine, dimethocaine/larocaine, piperocaine, propoxycaine, procaine/novocaine, proparacaine, tetracaine/amethocaine, lidocaine, articaine, bupivacaine, cinchocaine/dibucaine, etidocaine, levobupivacaine, lidocaine/lignocaine, mepivacaine, prilocaine, ropivacaine, trimecaine, lidocaine/prilocaine, lidocaine/tetracaine, prilocaine hydrochloride and epinephrine, lidocaine, bupivacaine, and epinephrine, iontocaine, septocaine, saxitoxin, neosaxitoxin, tetrodotoxin, menthol).

Prophylactic compounds can also include other components commonly used in lotions, creams and gels, such as fragrances, glycerol, petroleum jelly, dyes, preservatives, proteins, stabilizing agents, ferric oxide ($Fe_2O_3$), zinc carbonate, or mixtures thereof. Prophylactic agents can also include antioxidants. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Particularly preferred agents to be delivered include UV filters, such as padimate O (PO), zinc oxide (ZnO), titanium dioxide (TiO2), silicon oxide coated ZnO or $TiO_2$, avobenzone, tinosorb S, mexoryl SX, mexoryl XL, helioplex, octinoxate, octocrylene, oxybenzone, octisalate, homosalate, uvinul T 150, cinoxate, aminobenzoic acid, ensulizole, dioxybenzone, meradimate, sulisobenzone, trolamine salicylate, enzacamene, bisdisulizole disodium, uvinul A Plus, uvasorb HEB, parsol SLX, and amiloxate. Incorporated into microparticles, these agents may be used to prevent skin conditions and skin diseases.

2. Active Agents: Therapeutic Agents, Diagnostic Agents, Prophylactic Agents, Cosmetic Agents, Dyes and/or Nutraceuticals Additional agents to be delivered include cosmetic, therapeutic, nutritional, diagnostic, and prophylactic compounds. Proteins, peptides, carbohydrates, polysaccharides, nucleic acid molecules, and organic molecules, as well as diagnostic agents, can be delivered. The preferred materials to be incorporated are prophylactic agents, such as UV filters, anti-oxidants, anesthetics, corticosteroids, anti-acne agents, and vitamins Other preferred materials to be incorporated are therapeutic agents. Therapeutic agents include antibiotics, antivirals, anti-parasites (helminths, protozoans), anti-cancer (referred to herein as "chemotherapeutics", including cytotoxic drugs such as doxorubicin, cyclosporine, mitomycin C, cisplatin and carboplatin, BCNU, 5FU, methotrexate, adriamycin, camptothecin, epothilones A-F, and taxol), peptide drugs, anti-inflammatories, and nutraceuticals.

Representative classes of diagnostic materials include paramagnetic molecules, fluorescent compounds, magnetic molecules, and radionuclides. Exemplary materials include, but are not limited to, metal oxides, such as iron oxide, metallic particles, such as gold particles, etc. Biomarkers can also be conjugated to the surface for diagnostic applications.

One or more active agents may be formulated alone or with excipients or encapsulated on, in or incorporated into the microparticles or nanoparticles. Active agents include therapeutic, prophylactic, neutraceutical and diagnostic agents. Any suitable agent may be used. These include organic compounds, inorganic compounds, proteins, polysaccharides, nucleic acids or other materials that can be incorporated using standard techniques.

For imaging, radioactive materials such as Technetium99 ($^{99m}$Tc) or magnetic materials such as $Fe_2O_3$ could be used. Examples of other materials include gases or gas emitting compounds, which are radioopaque.

Examples of active agents include sunblock/sunscreen agents, such as oxybenzone, dioxybenzone, octinoxate, homosalate, octisalate, octocrylene, avobenzone, mexoryl SX, padimate O, p-aminobenzoic acid (PABA), phenylbenzimidazole sulfonic acid, cinoxate, menthyl anthranilate, sulisobenzone, parsol compounds, tinosorb compounds, and heliopan compounds, and non-chemical sunblock agents such as zinc oxide, titanium dioxide, and pigments/melanin/melanin derivatives; agents for anti-aging, for cellular/DNA damage prevention, prevention of pre-malignant conditions, such as actinic keratosis, skin cancer prevention and include natural/herbal antioxidants include curcumin, lycopene, lutein, and alpha-lipoic acid (ALA), ascorbic acid (vitamin C), vitamin A, vitamin B3, vitamin E, beta-carotene, nicotinomide, selenium and zinc, soy-derived genistein, resveratrol, retinols and retinoids, superoxide dismutase (SOD), catalase (CAT), glutathione peroxidase (GSHpx), glutathione reductase, nitric oxide synthases (NOS-1,-2,-3), inhibitors of tumor promoting growth factors, such as inhibitors of epidermal growth factors, e.g. EDGF, KGF; and IGF, inhibitors of tumor-promoting cytokines, e.g. interleukin-22, GRO-1, and AREG, CYP1B1, direct and specific inhibitors of CYP1B1, general inhibitors of P450 enzymes, and inhibitors of the aryl hydrocarbon receptor (AHR), as well as CYP1A1 and its inducers, and other metabolizing agents that detoxify active mutagens/carcinogens.

Examples of anti-pathogen (anti-bacterial, anti-viral, anti-fungal) and microbiome altering agents include vancomycin and other antibiotics used specifically to treat MRSA, triclosan, silver (ionic), benzoyl peroxide, other related agents, and bacterial nitric oxide synthase (NOS) inhibitors, anti-fungal agent nitric oxide (NO) and NO releasing solutions, and anti-viral agents acyclovir, famcyclovir, and valacyclovir Anti-inflammatory agents include corticosteroids and non-steroidal anti-inflammatory drugs (NSAIDs) such as aspirin and ibuprofen, Jak and/or Stat inhibitors, and dapsone.

Anti-acne agents include benzyol peroxide, retinoids, including tretinoin, and dapsone, and tumor necrosis factor-alpha (TNF-α) inhibitors and other anti-inflammatory agents.

Agents for stimulation of hair growth to treat conditions that cause alopecia, including androgenetic alopecia, alopecia areata, traction alopecia, scarring alopecia, and lichen planopilaris, include growth factors, such as fibroblast growth factors (FGFs), KFG (keratinocyte growth factors), EDGFs (epidermal derived growth factors), inhibitors of dihydrotestosterone (DHT) receptor, and other hormone and hormone receptors, anti-inflammatory agents, including TNF-α inhibitors, non-steroidal anti-inflammatories ("NSAIDs"), Jak and/or Stat inhibitors, and NKG2D inhibitors.

Structural or enzymatic proteins can be incorporated into BNPs for the treatment and/or prevention of cutaneous diseases, such as filaggrin for atopic dermatitis or ichthyosis vulgaris, transglutaminase for autosomal-recessive congenital ichthyosis (ARCI), collagen VII for dystrophic epidermolysis bullosa (DEB), keratin 5 and/or 14 for epidermolysis bullosa simplex (EBS), and keratin 1 and/or 10 for bullous congenital ichthyosiform erythroderma (BCIE).

Agents for stimulation of wound healing include growth factors, collagen, antibodies, extracellular matrix materials, fibrinogen and other products for the stimulation of vascular elements, collagen production, and/or keratinocyte migration and proliferation.

Agents for cosmetic use include pigments/dyes/minerals and other ingredients, optionally further including filters or blockers of ultraviolet light. In addition, agents such as fragrance oils and additives may be used.

Agents for use as pesticides/insect repellents include DEET (N,N-diethyl-m-toluamide), natural/essential oil insect repellents such as citronella oil, Neem oil, birch tar, and bog myrtle, and permethrin.

Alternatively, the biodegradable polymers may encapsulate cellular materials, such as for example, cellular materials to be delivered to antigen presenting cells as described below to induce immunological responses.

Cell-mediated immunity is needed to detect and destroy virus-infected cells. Most traditional vaccines (e.g. protein-based vaccines) can only induce humoral immunity. DNA-based vaccine represents a unique means to vaccinate against a virus or parasite because a DNA based vaccine can induce both humoral and cell-mediated immunity. In addition, DNA-based vaccines are potentially safer than traditional vaccines. DNA vaccines are relatively more stable and more cost-effective for manufacturing and storage. DNA vaccines consist of two major components—DNA carriers (or delivery vehicles) and DNAs encoding antigens. DNA carriers protect DNA from degradation, and can facilitate DNA entry to specific tissues or cells and expression at an efficient level.

3. Targeting Moieties

The PG coated particles can be modified to facilitate targeting or adhesion through the attachment of targeting molecules. Exemplary target molecules include proteins, peptides, nucleic acids, lipids, saccharides, or polysaccharides, or small molecules that bind to one or more targets associated with an organ, tissue, cell, or extracellular matrix. For example, a targeting moiety can be a polypeptide, such as an antibody that specifically recognizes a cell marker that is present exclusively or in higher amounts on a target cell (e.g., a keratinocyte cell antigen).

Targeting molecules can be covalently bound to particles using a variety of methods known in the art. In some embodiments, the targeting moieties are covalently associated with the polymer, preferably via a linker cleaved at the site of delivery.

The nanoparticles can contain one or more polymer conjugates containing end-to-end linkages between the polymer and a targeting element or a detectable label. For example, a modified polymer can be a PLA-HPG-peptide block polymer.

Examples of targeting moieties include peptides such as iRGD, LyP1; small molecule such as folate, aptamers and antibodies, such as antibodies to integrins or skin cell receptors, or their combinations at various molar ratios.

The targeting element of the nanoparticle can be an antibody or antigen binding fragment thereof. The targeting elements should have an affinity for a cell-surface receptor or cell-surface antigen on the target cells and result in binding of the particle to the target cell.

The target molecule can be a cell surface polypeptide, lipid, or glycolipid. Cell specific markers can be for specific types of cells including, but not limited to stem cells, skin cells, follicle cells, and infected skin cells. The cell markers can be specific for endothelial, ectodermal, or mesenchymal cells. Representative cell specific markers include, but are not limited to, cancer specific markers.

The targeting element can be a peptide. Specifically, the plaque targeted peptide can be, but is not limited to, one or more of the following: RGD, iRGD(CRGDK/RGPD/EC), LyP-1, P3(CKGGRAKDC), or their combinations at various molar ratios. The targeting peptides can be covalently associated with the polymer and the covalent association can be mediated by a linker.

The targeting element can be an antibody or an antigen-binding fragment thereof. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. The antigen binding portion of the antibody can be any portion that has at least one antigen binding site, such as Fab, $F(ab')_2$, dsFv, sFv, diabodies, and triabodies. In certain embodiments, the antibody is a single chain antibody.

Aptamers are oligonucleotide or peptide sequences with the capacity to recognize virtually any class of target molecules with high affinity and specificity. Aptamers bind to targets such as small organics, peptides, proteins, cells, and tissues. Unlike antibodies, some aptamers exhibit stereoselectivity. The aptamers can be designed to bind to specific targets expressed on cells, tissues or organs.

The outer surface of the particle may be treated using a mannose amine, thereby mannosylating the outer surface of the particle. This treatment may cause the particle to bind to the target cell or tissue at a mannose receptor on the antigen presenting cell surface. Alternatively, surface conjugation with an immunoglobulin molecule containing an Fc portion (targeting Fc receptor), heat shock protein moiety (HSP receptor), phosphatidylserine (scavenger receptors), and lipopolysaccharide (LPS) are additional receptor targets on cells or tissue.

The attachment of any positively charged ligand, such as polyethyleneimine or polylysine, to any particle may improve bioadhesion due to the electrostatic attraction of the cationic groups coating the beads to the net negative charge of the mucus. The mucopolysaccharides and mucoproteins of the mucin layer, especially the sialic acid residues, are responsible for the negative charge coating. Any ligand with a high binding affinity for mucin could also be covalently linked to most microparticles with the appropriate chemistry. For example, polyclonal antibodies raised against components of mucin or else intact mucin, when covalently coupled to particles, would provide for increased bioadhesion. The ligand affinity need not be based only on electrostatic charge, but other useful physical parameters such as solubility in mucin or else specific affinity to carbohydrate groups.

The attachment of polyamino acids containing extra pendant carboxylic acid side groups, e.g., polyaspartic acid and polyglutamic acid, should also provide a useful means of increasing bioadhesiveness. Using polyamino acids in the 15,000 to 50,000 kDa molecular weight range would yield chains of 120 to 425 amino acid residues attached to the surface of the particles. The polyamino chains would increase bioadhesion by means of chain entanglement in mucin strands as well as by increased carboxylic charge.

4. Sheddable Polyethylene Glycol (PEG) Coatings

The HP coating can be modified by attaching PEG to the surface of the coating. For example, HPG-coated particles can be modified by covalently attaching PEG to the surface. This can be achieved by converting the vicinyl diol groups to aldehydes and then reacting the aldehydes with functional groups on PEG, such as aliphatic amines, aromatic amines, hydrazines and thiols. The linker has end groups such as aliphatic amines, aromatic amines, hydrazines, thiols and O-substituted oxyamines. The bond inserted in the linker can be disulfide, orthoester and peptides sensitive to proteases.

PEG with a functional group or a linker can form a bond with aldehyde on PLA-HPGALD and reversed the bioadhesive(sticky) state of PLA-HPGALD to stealth state. This bond or the linker is labile to pH change or high concentration of peptides, proteins and other biomolecules. "ALD" denotes an aldehyde. After administration systematically or locally, the bond attaching the PEG to PLA-HPGALD can be reversed or cleaved to release the PEG in response to environment and exposed the PLA-HPGALD particles to the environment. Subsequently, the particles will interact with the tissue and attach the particles to the tissues or extracellular materials such as proteins. The environment can be acidic environment in tumors, reducing environment in tumors, protein rich environment in tissues.

III. Methods of Making Particles and Modification Thereof

A. Methods of Making Polymeric Particles

Methods of making polymeric particles are known in the art. Common microencapsulation techniques include, but are not limited to, spray drying, interfacial polymerization, hot melt encapsulation, phase separation encapsulation (spontaneous emulsion microencapsulation, solvent evaporation microencapsulation, and solvent removal microencapsulation), coacervation, low temperature microsphere formation, and phase inversion nanoencapsulation (PIN). A brief summary of these methods is presented below.

In some embodiments, the particles are prepared using an emulsion-based technique. In particular embodiments, the particles are prepared using a double emulsion solvent evaporation technique. For example, the amphiphilic material and the hydrophobic cationic material are dissolved in a suitable organic solvent, such as methylene chloride or dichloromethane (DCM), with or without agent to be encapsulated.

1. Phase Separation Microencapsulation

In phase separation microencapsulation techniques, a polymer solution is stirred, optionally in the presence of one or more active agents to be encapsulated. While continuing to uniformly suspend the material through stirring, a non-solvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the active agent(s) in a droplet with an outer polymer shell.

2. Spontaneous Emulsion Microencapsulation

Spontaneous emulsification involves solidifying emulsified liquid polymer droplets formed above by changing temperature, evaporating solvent, or adding chemical cross-linking agents. The physical and chemical properties of the encapsulant, as well as the properties of the one or more active agents optionally incorporated into the nascent particles, dictates suitable methods of encapsulation. Factors such as hydrophobicity, molecular weight, chemical stability, and thermal stability affect encapsulation.

3. Solvent Evaporation Microencapsulation

Methods for forming microspheres using solvent evaporation techniques are described in E. Mathiowitz et al., J. Scanning Microscopy, 4:329 (1990); L. R. Beck et al., Fertil. Steril., 31:545 (1979); L. R. Beck et al, Am. J Obstet. Gynecol., 135(3) (1979); S. Benita et al., J. Pharm. Sci., 73:1721 (1984); and U.S. Pat. No. 3,960,757 to Morishita et al. The polymer is dissolved in a volatile organic solvent, such as methylene chloride. One or more active agents to be incorporated are optionally added to the solution, and the mixture is suspended in an aqueous solution that contains a surface active agent such as poly(vinyl alcohol). The resulting emulsion is stirred until most of the organic solvent evaporated, leaving solid microparticles/nanoparticles. This method is useful for relatively stable polymers like polyesters and polystyrene.

4. Phase Inversion Nanoencapsulation (PIN)

Nanoparticles can also be formed using the phase inversion nanoencapsulation (PIN) method, wherein a polymer is dissolved in a "good" solvent, fine particles of a substance to be incorporated, such as a drug, are mixed or dissolved in the polymer solution, and the mixture is poured into a strong non solvent for the polymer, to spontaneously produce, under favorable conditions, polymeric microspheres, wherein the polymer is either coated with the particles or the particles are dispersed in the polymer. See, e.g., U.S. Pat. No. 6,143,211 to Mathiowitz, et al. The method can be used to produce monodisperse populations of nanoparticles and microparticles in a wide range of sizes, including, for example, about 100 nanometers to about 10 microns.

5. Microfluidics

Nanoparticles can be prepared using microfluidic devices. A polymeric material is mixed with a drug or drug combinations in a water miscible organic solvent. The water miscible organic solvent can be one or more of the following: acetone, ethanol, methanol, isopropyl alcohol, acetonitrile and Dimethyl sulfoxide (DMSO). The resulting mixture solution is then added to an aqueous solution to yield nanoparticle solution.

B. HP Conjugates or Coatings

Hyperbranched polymers including, but not limited to, polyglycerol (HPG) can be covalently bound to one or more materials, such as a polymer, that form the core of the particles using methodologies known in the art. For example, an HP such as HPG can be covalently coupled to a polymer having carboxylic acid groups, such as PLA, PGA, or PLGA using DIC/DMAP. The HPG can be initiated hydroxyl, amine, and carboxylate terminated molecules, such as an alcohol with one or multiple long hydrophobic tails. In another example, the HP, such as HPG, can be initiated from special functionalized initiators to facilitate the conjugation to more materials. These special initiators include disulfide (Yeh et al., *Langmuir.* 24(9):4907-16 (2008)).

Figure 1B:
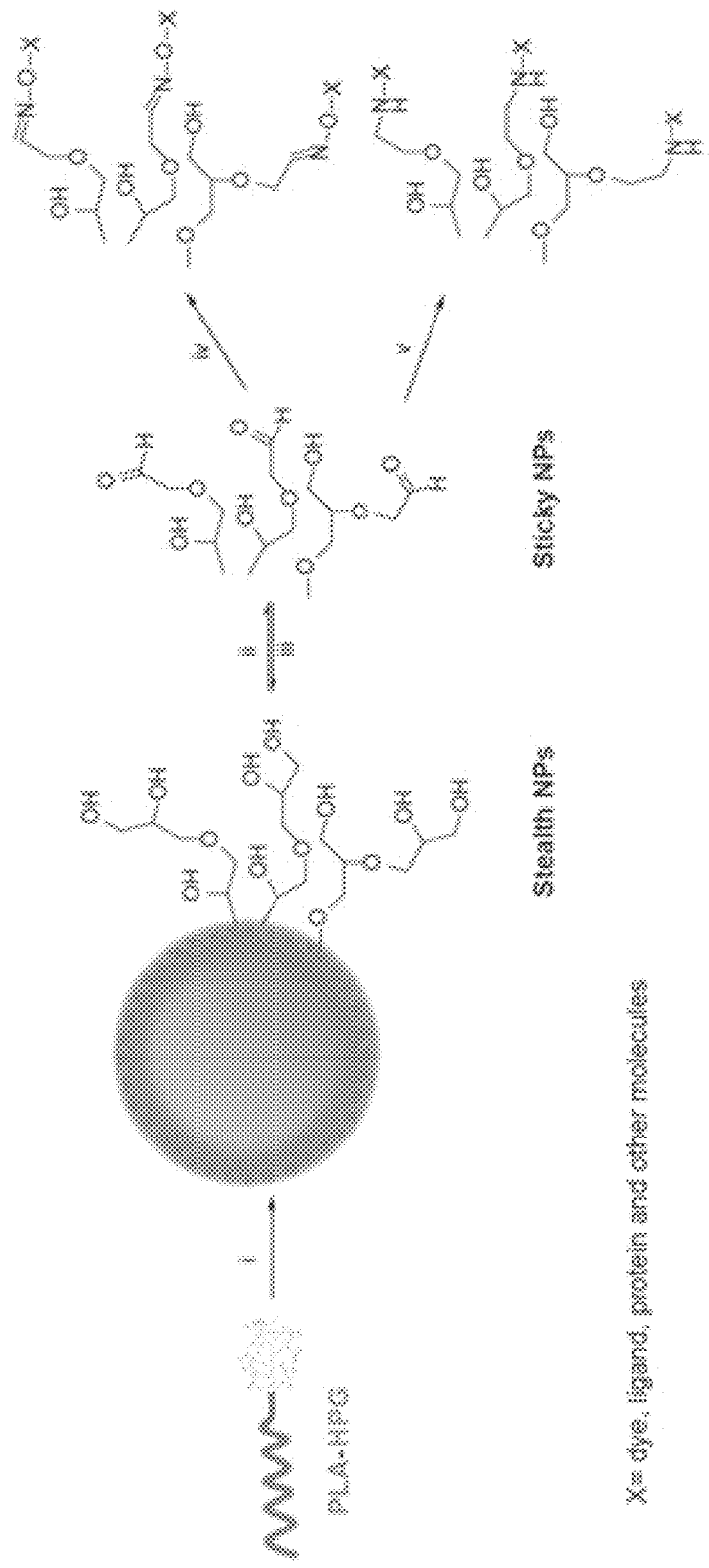
FIG. 1B is a schematic showing the synthesis of stealth nanoparticles and sticky nanoparticles.

The HPG can be functionalized to introduce one or more reactive functional groups that alter the surface properties of the particles. For example, HPG-coated particles prevent non-specific adsorption of serum proteins and increase the blood circulation of the particles. Such particles are referred to as stealth particle. However, the hydroxyl groups on HPG can be chemically modified to cause the particles to stick to biological material, such as tissues, organs, cells, etc. Such functional groups include aldehydes, amines, O-substituted oximes, and combinations thereof. A synthetic scheme for such chemical conversions is shown in FIG. 1.

The surface of the particles can further be modified with one or more targeting moieties or covalently bound to an HP such as HPG via a coupling agent or spacer in organic solvents such as dichloromethane (DCM), dimethylformamide (DMF), dimethyl sulfoxide (DMSO) or tetrahydrofuran (THF), diisopropylcarbodiimide (DIC), 4-(N,N-dimethylamino)pyridine (DMAP), dicyclohexylcarbodiimide (DCC), DIC/DMAP, DCC/DMAP, acylchloride/pyridine. In some embodiments, the polymer is functionalized/modified before nanoparticle formation. Alternatively, the targeting moieties may be attached to NPs after the synthesis of NPs in aqueous solution (or other protic solution such as alcohol). As discussed in more detail below, HPG coated NPs can be transformed to aldehyde terminated NPs by $NaIO_4$ treatment (or carboxylic acid terminated by $NaIO_4$ treatment followed by sodium chlorite treatment) so the targeting moieties may be directly covalently attached to NPs via aldehyde (or carboxylic acid) groups on NPs and functional groups (amine, hydrazine, amino-oxy and their derivatives) on the targeting moieties or indirectly attached to the NPs via coupling agents or spacers (such as amino-oxy modified biotin and cysteine).

Certain properties of the PLA-HPG conjugate are important for the observed effects thereof. Because high molecular weight HPG has better resistance to non-specific adsorption to biomolecules, the low molecular weight components can be removed from the synthesized HPG by multiple solvent precipitations and dialysis.

In the preferred embodiment, a polyhydroxy acid such as PLA is selected as the hydrophobic core material because it is biodegradable, has a long history of clinical use, and is the major component of a NP system that is advancing in clinical trials. To covalently attach the PLA to HPG, the previous approach was to first functionalize the HPG with an amine and then conjugate the carboxylic group on PLA to the amine. This approach is efficient but cannot be used to make HPG as surface coatings since any amines that do not react with PLA will lead to a net positive charge on the neutral HPG surface and reduce the ability of HPG to resist adsorption of other molecules on the surface. To avoid this, a one-step esterification between PLA and HPG can be employed, which maintains the charge neutral state of the HPG.

Targeting molecules or agents to be encapsulated or delivered may be associated with the surface of, encapsulated within, surrounded by, and/or distributed throughout the polymeric matrix of the particles.

C. Particle Properties

The particles may have any zeta potential. The particles can have a zeta potential from −300 mV to +300 mV, −100 mV to +100 mV, from −50 mV to +50 mV, from −40 mV to +40 mV, from −30 mV to +30 mV, from −20 mV to +20 mV, from −10 mV to +10 mV, or from −5 mV to +5 mV. The particles can have a negative or positive zeta potential. In some embodiments the particles have a substantially neutral zeta potential, i.e. the zeta potential is approximately 0 mV. In preferred embodiments the particles have a zeta potential of approximately −30 to about 30 mV, preferably from about −20 to about 20 mV, more preferably from about −10 to about 10 mV.

The particles may have any diameter. The particles can have a diameter of about 1 nm to about 1000 microns, about 1 nm to about 100 microns, about 1 nm to about 10 microns, about 1 nm to about 1000 nm, about 1 nm to about 500 nm, about 1 nm to about 250 nm, or about 1 nm to about 100 nm. In preferred embodiments, the particle is a nanoparticle having a diameter from about 25 nm to about 250 nm. In more preferred embodiments, the particles are nanoparticles having a diameter from about 180 nm to about 250 nm, preferably from about 180 nm to about 230 nm.

The polydispersity is from about 0.05 to 0.30, preferably from about 0.05 to about 0.25, more preferably from about 0.05 to about 0.20, more preferably from about 0.05 to about 0.15, most preferably from about 0.05 to about 0.10.

IV. Topical Formulations

The particles can be formulated with appropriate pharmaceutically acceptable carriers into pharmaceutical compositions for administration to an individual in need thereof. The formulations can be administered topically (e.g., to the skin via non-invasive topical application). Other routes of administration include, but are not limited to, transdermal.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, POLOXAMER® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, benzalkonium, sorbic acid, and thimerosal. The formulation may also contain an antioxidant to prevent degradation of the active agent(s). Water soluble polymers may be used in formulations. Suitable water-soluble polymers include, but are not limited to, polyvinylpyrrolidone, dextran, carboxymethylcellulose, and polyethylene glycol.

Carrier also includes all components of the coating composition which may include polymerizers, pigments, colorants, stabilizing agents, and glidants. Formulations can be prepared using one or more topical or pharmaceutically acceptable excipients, including diluents, preservatives, binders, lubricants, disintegrators, swelling agents, fillers, stabilizers, and combinations thereof.

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

The topical formulations may contain an effective amount of the one or more non-bioadhesive and bioadhesive nanoparticles and microparticles delivering an effective amount of the one or more agents incorporated therein.

Suitable topical formulations include creams, ointments, salves, sprays, gels, lotions, irrigants, and emulsions.

"Buffers" are used to control pH of a formulation. Preferably, the buffers buffer the formulation from a pH of about 4 to a pH of about 7.5, more preferably from a pH of about 4 to a pH of about 7, and most preferably from a pH of about 5 to a pH of about 7. In a preferred embodiment, the buffer is triethanolamine.

"Emollients" are an externally applied agent that softens or soothes skin and are generally known in the art and listed in compendia, such as the "Handbook of Pharmaceutical Excipients", 4$^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

"Penetration enhancers" are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

"Preservatives" can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

A. Emulsions

An emulsion is a preparation of one liquid distributed in small globules throughout the body of a second liquid. In particular embodiments, the non-miscible components of the emulsion include a lipophilic component and an aqueous component. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

B. Lotions

A lotion can contain finely powdered substances that are insoluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

C. Creams

Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments, as they are generally easier to spread and easier to remove.

The difference between a cream and a lotion is the viscosity, which is dependent on the amount/use of various oils and the percentage of water used to prepare the formulations.

D. Ointments

Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy than ointments prepared with the same components.

E. Gels

Gels are semisolid systems containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alkylene glycols, such as propylene glycol; dimethyl isosorbide; alcohols, such as isopropyl alcohol and ethanol. The solvents are typically selected for their ability to dissolve the compound. Other additives, which improve the skin feel and/or emolliency of the formulation, may also be incorporated. Examples of such additives include, but are not limited to, isopropyl myristate, ethyl acetate, $C_{12}$-$C_{15}$ alkyl benzoates, mineral oil, squalane, cyclomethicone, capric/caprylic triglycerides, and combinations thereof.

F. Foams

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases, which can produce flammable or explosive vapors during spraying. Furthermore, the compositions preferably contain no volatile alcohols, which can produce flammable or explosive vapors during use.

V. Methods of Using Particles and Formulations

The particles can be used for a variety of applications including protecting tissue from UV light, therapeutic, prophylactic, cosmetic, diagnostic agent delivery, tissue engineering, etc. In some embodiments, the particles are "stealth" particles, where the hydroxyl groups on HP resist non-specific protein absorption. This can allow targeted particles to be delivered to the desired site for drug release. Such stealth properties can also be useful for topical delivery, for example, diffusion into hair follicles to release agents to promote hair growth/prevent hair loss or agents that promote hair loss. Alternatively, the vicinyl diol groups can be converted to functional groups that adhere to biological materials, such as tissue (e.g., cornea), organs (e.g., skin), cells, proteins, etc. Such particles are referred to as "sticky".

The particles can be used to deliver one or more therapeutic agents, diagnostic agents, prophylactic agents, nutraceuticals, or combinations thereof to the skin. As discussed above, the vicinyl diol groups on HP can be chemically transformed to functional groups that make the particle adhere or stick to tissue or other biological materials, such as skin (e.g., sticky particles). For example, incubation of HPG-coated particles with the reagent $NaIO_4$, which converts vicinyl diol groups to aldehyde groups, showed an estimated 8 aldehyde groups/$nm^2$ after about 20 minutes. Surface immobilization of HPG particles on lysine-coated slides increased as the incubation time with $NaIO_4$ increased.

Aldehyde-functionalized HPG-coated particles loaded with the dye DiD were incubated with pig skin for 6 hours. The relative fluorescence of the aldehyde-functionalized particles was three-fold higher than the relative fluorescence of HPG-coated particles.

The compositions are most typically formulated for topical delivery and can be, for example, applied to the skin, hair, etc., of a subject in need thereof. In some embodiments, the formulations are delivered percutaneously via incorporation of pharmacologic active ingredients into BNPs and/or NNPs, and penetration into the skin cells and extracellular matrix of the epidermis, dermis, subcutaneous fat, follicules, acrosyngium, inflammatory lesions, benign and malignant cutaneous neoplasms, metastatic cutaneous neoplasms, aging and/or photodamaged skin, and normal skin.

Delivery of BNPs and/or NNPs can be accomplished by direct application to the skin in various permeation enhancement vehicle formulations, including liposomal and methyl methacrylate/glycol dimethacrylate crosspolymers, occlusive dressings, jet injector (air, helium, nitrogen, water, saline, or other vehicle), laser generated micropores (as in fractionated laser), microneedle generated pores, or frank needle/syringe inoculation. BNPs and NNPs formulations can (1) provide a depot and controlled release of the active pharmacologic ingredients, 2) enhance their uptake by cells or tumor cells to increase efficacy, and/or (3) increase stability and shelf-life and performance.

BNPs sunscreen formulations can afford the advantages detailed above for NNP and NP sunscreen formulations, while also providing for the major advantage of bioadherence to the skin and increased substantivity and performance. Thus in some embodiments, the active agent penetrate the skin effectively, while in some embodiments skin penetration is delayed or reduced, such that the active agents at or near the surface of the skin.

1. Sunscreens

In some embodiments, the particles can be used as or formulated in a sunscreen or sunblock. Use of the disclosed particles can improve sunscreen formulation via the utilization of biodegradable nanoparticle encapsulation of active ingredients that absorb and/or reflect UV light. In some embodiments, NNP and (general biodegradable) NP sunscreen formulations can (1) prevent or inhibit or minimize the absorption of sunscreen agents into the skin and bloodstream, (2) prevent or inhibit or minimize the interactions and reactivity of these sunscreen agents with themselves or other sunscreen agents in the formulations to help increase stability and shelf-life and performance.

BNPs sunscreen formulations can afford the advantages detailed above for NNP and NP sunscreen formulations, while also providing for the major advantage of bioadherence to the skin thereby increasing substantivity and performance.

For example, in some embodiments a sunscreen or sunblock includes formulation includes, for example by incorporation into particles (e.g., NPs, NNPs, BNPs, or any other biodegradable nanoparticle formulations (PLA, PLG, PLGA, PCA, PCL, PAC, chitosan, gelatin), one or more chemical sunscreen agents including, but not limited to, oxybenzone, dioxybenzone, meradimate, amiloxate, octinoxate, homosalate, octisalate, octocrylene, sulisobenzone, avobenzone, ecamsule, ensulizole, enzacamene, bisdisulizole disoidium, padimate O, p-aminobenzoic acid (PABA), phenylbenzimidazole sulfonic acid, cinoxate, trolamine salicylate, menthyl anthranilate, sulisobenzone, parsol compounds, tinosorb compounds, heliopan compounds, and combinations thereof.

Additionally or alternatively, the formulation includes, for example by incorporation into particles (e.g., NPs, NNPs, BNPs, or any other biodegradable nanoparticle formulations (PLA, PLG, PLGA, PCA, PCL, PAC, chitosan, gelatin), one or more non-chemical sunscreen agents into NPs, NNPs, BNPs, or any other biodegradable nanoparticle formulations (PLA, PLG, PLGA, PCA, PCL, PAC, chitosan, gelatin), including but not limited to zinc oxide, titanium dioxide, and combinations thereof.

Additionally or alternatively, the formulation includes, for example by incorporation into particles (e.g., NPs, NNPs, BNPs, or any other biodegradable nanoparticle formulations (PLA, PLG, PLGA, PCA, PCL, PAC, chitosan, gelatin), one or more natural anti-oxidant and/or other UV absorbing agents, including but not limited to polyohenols, indegoids, retinoids, melanin and melanin derivatives, ascorbic acid, citric acid, oxalic acid, phytic acid, Polypodium leucotomos extract, carrageenan, milk thistle extract, coenzyme Q10, zinc gluconate, bioflavonoids, isoflavones, other flavones and flavonols, luteins, lycopenes, konjac, alpha lipoic acid, beta carotene, grape seed extract, alpha-tocopherol acetate, niacinamide, nicotinomide, green tea extract, copper gluconate, resveratrol and other stilbenoids, cholecalciferol, sodium Selenite/selenium, bilberry fruit, folic acid, astaxanthin (red algae extract), canthaxanthin, zeaxanthin, anthocyanins and other cyanins, cinnamic acid and other cinnamates, salicylic acid, curcumin, other suitable agents discussed herein, and combination thereof.

In preferred embodiments, sunblock formulations are made by incorporation of chemical sunscreen agents into BNPs, such as oxybenzone, dioxybenzone, octinoxate, homosalate, octisalate, octocrylene, avobenzone, mexoryl SX, padimate O, p-aminobenzoic acid (PABA), phenylbenzimidazole sulfonic acid, cinoxate, menthyl anthranilate, sulisobenzone, parsol compounds, tinosorb compounds, and heliopan compounds, and non-chemical sunscreen agents such as zinc oxide, titanium dioxide. The BNPs can also be used in topical formulations for artificial skin tanners.

Pigments/minerals/melanin/melanin derivatives can be incorporated, optionally along with agents for protection against ultraviolet light exposure as well as for cosmetic uses, including by direct manual application to the skin and by spray applications.

As demonstrated by the examples, particles were loaded with padimate O (PO), an organic compound used in sunscreens. Under conditions mimicking the pH range of human sweat (4.5 and 7.4), the particles retained more than about 96% of the PO after 20 hours. The particles also exhibited UV absorption compared to PO dispersed in water or aqueous buffer.

2. Cosmetics

The NNPs and BNPs can be used in topical formulations for cosmetic application by incorporating of pigments, dyes, minerals, latex, silicon, and other ingredients and other ingredients, optionally further including protection against ultraviolet light exposure. These can be directly applied to the skin as a spray, liquid or foundation, concealer, eye liner, eye shadow, mascara, lip coloring/glossing. These are especially useful for treatment of fine and deep lines, grooves, and rhytides.

NNPs and BNPs may also be used to target hair follicles, hair bulges and hair roots to deliver coloring, therapeutic, antiseptic, or neutraceutical agents. Hair coloring dyes, holding products and hair thickening agents, such as dyes, pigment, minerals, adhesives, may also be incorporated into BNPs, which can be applied directly to the hair or by spray or foam applications. The BNPs incorporating pigment can also be used in ink for temporary or permanent tattoos when applied to the skin or to hair.

3. Fragrances

The NNPs and BNPs can be used for topical formulations for application to the skin to enhance and emanate fragrances, or suppress or neutralize odors. The topical formulations can be used as fragrances, perfumes, colognes, after-shave products by incorporation of fragrances into BNPs for the protections against penetration into the skin thereby decreasing risk of irritancy and allergic reaction. The topical formulations may also be useful in hyperhydrosis control and for use as antiperspirants and deodorants.

4. Skin Repair and Anti-Aging Products

In another preferred embodiment, anti-aging and cellular/DNA damage prevention, pre-malignant (actinic keratosis), skin cancer prevention and anti-aging/skin cancer prevention formulations are made by incorporation of anti-oxidants (alone or in combination with sunblock agents) into BNPs or NNPs. Examples of natural/herbal antioxidants include curcumin, lycopene, lutein, and alpha-lipoic acid (ALA). Examples of vitamins and their derivatives include ascorbic acid (vitamin C), vitamin A, vitamin B3, vitamin E, beta-carotene, and nicotinomide. Examples of minerals include selenium and zinc. Examples of useful polyphenols include soy-derived genistein. Other dietary agents/supplements include resveratrol, retinols and retinoids. Examples of useful enzymes include superoxide dismutase (SOD), catalase (CAT), glutathione peroxidase (GSHpx), glutathione reductase, nitric oxide synthases (NOS-1,-2,-3). Examples of useful anti-aging/skin cancer prevention compounds factors (alone or in combination with sunblock agents) include anti-tumor promoting growth, inhibitors of epidermal growth factors, e.g. EDGF, KGF; and IGF, inhibitors of tumor-promoting cytokines, e.g. interleukin-22, GRO-1, and AREG, CYP1B1, direct and specific inhibitors of CYP1B1, general inhibitors of P450 enzymes, and inhibitors of the aryl hydrocarbon receptor (AHR), as well as CYP1A1 and its inducers, and other metabolizing agents that detoxify active mutagens/carcinogens. Other agents include agents for treating skin aging, such as anti-reactive oxygen species (ROS) therapies.

5. Hair Products

The particles can also be used to deliver agents to hair follicles, for examples, agents to promote hair growth or reduce hair loss or therapies to remove hair. The stealth nature of the particles can allow diffusion of the particles into the hair follicles. The particles can also be used to deliver products to the hair shafts, to strengthen the hair and prevent damage/breakage, and to prevent and/or treat hair shaft infections including lice.

Topical formulations may be used in hair coloring and styling, as the NNPs and/or BNPs may incorporate hair dyes, pigments, minerals, holding products, thickening agents, adhesives. The topical formulations for use in hair styling or coloring may be applied directly using manual application to the hair or by spray or foam applications. Alternatively, the topical formulations may include NNPs and/or BNPs that mask the skin during hair coloring to protect the skin from the hair dye.

6. Wound Healing

A chronic wound is a wound that does not heal normally. Wounds that do not heal within three months are often considered chronic. One embodiment provides administering an effective amount of the particles to a chronic wound to promote or enhance healing.

The disclosed particles can also be used to treat fibrotic wounds. Fibrotic wounds have dysregulated healing and typically delayed healing. Fibrosis can be defined as the replacement of the normal structural elements of the tissue by distorted, non-functional and excessive accumulation of scar tissue. One embodiment provides a method for treating fibrotic wounds by administering an effective amount of the disclosed particles to promote or enhance fibrotic wound healing.

The particles can also be used with wound dressings. One embodiment provides a wound dressing having a layer of particles on the wound dressing. The layer of particles is configured to come into contact with the wound when the wound dressing is applied to a wound. The particles can be impregnated in the wound dressing or coated on the wound dressing using conventional techniques. The wound dressing can be made of absorbent materials such as cotton or fleece. The wound dressing can also be made of synthetic fibers, for example, polyamide fibers. In certain embodiments, the wound dressing can have multiple layers including an adhesive layer, an absorbent layer, and moisture regulation layer. The wound dressing can also include antimicrobial agents, antifungal agents, and other active agents to promote wound healing such as cytokines and growth factors discussed above.

Another embodiment provides a method for treating a wound by administering an effective amount of the disclosed particles to the wound to promote or induce hemostasis and then applying a wound dressing to the wound.

The advantage of these particles is that they adhere to the skin and/or applied material, where they are retained at the site of injury to provide sustained treatment. Mixtures releasing different amounts or different drugs at different times are particularly advantageous for treatment of wounds such as diabetic wound ulcers. Ligands can be selected to enhance the particles being retained at the site, by binding to extracellular matrix or through non-specific electrostatic binding.

Topical formulations for stimulation of wound healing can incorporate agents such as growth factors, collagen, antibodies, extracellular matrix materials, fibrinogen and other products for the stimulation of wound healing, including that induced by trauma, surgical, diabetic, vascular occlusive, and/or chemical or thermal burn) via the stimulation of vascular elements, collagen production, and/or keratinocyte migration and proliferation. These can be administered alone or in combination with the anti-infective (antibacterial, antiviral or antifungal) formulations discussed above).

7. Anti-Infective Formulations

Examples of anti-pathogen (anti-bacterial, anti-viral, anti-fungal) and microbiome altering formulations include topical formulations incorporating agents for the prevention and/or treatment of cutaneous bacterial infections, as well as the alteration of skin bacterial colonization and alterations to the normal/current state of skin flora. These may be useful for the treatment and/or prevention of impetigo, bacterial folliculitis, cellulitis (typically due to, but not limited to, *Staphylococcal* and *Streptococcal* ssp.), hot tub folliculitis (typically due to, but not limited to, *Pseudomonas* ssp.), pre- and post-procedure prevention of infections, by application to sites of skin for biopsy, surgery (including arthroscopic and laparoscopic), or other invasive procedures that access via the skin. The formulations may be particularly applicable to the prevention and/or treatment of methicillin-resistant *Staphylococcus aureus* (MRSA) infections, as it relates to the incorporation of antibiotics generally, and specifically as it relates to the incorporation of agents that are not typically used in topical applications due to their toxicity, limited penetration into the skin, and/or inability to persist on the skin.

Anti-fungal agents can be incorporated into BNPs or NNPs for the prevention and/or treatment of cutaneous fungal infections, as well as the alteration of skin fungal colonization and alterations to the normal/current state of skin flora, such as tinea corporis, tinea pedis, tinea capitas, tinea barbae, toe nail fungal infections (tinea unguium), Candidal infections, including intertrigo (e.g. inframammary, inguinal, gluteal), perleche/angular chelitis, vaginal moniliasis, balanitis, and *Pityrosporum* infections/overgrowth states (e.g. pityriasis versicolor, *pityrosporum* folliculitis.

Topical formulations incorporating anti-viral agents such as acyclovir, famcyclovir, and valacyclovir, into BNPs or NNPs can be used for the prevention and/or treatment of cutaneous viral infections/reactivation, including Herpes simplex virus (HSV) by application to lips, genitals and surrounding areas; Varicella zoster virus (VZV) by application to prior and/or suspected dermatomal eruptions, and Human papilloma virus (HPV) related conditions (warts, including genital warts; HPV related intraepithelial neoplasia/carcinoma, including oral, cervical, genital cancers) by application to prior and/or suspected lesions. Anti-viral agents can also be incorporated into BNPs or NNPs for the prevention of systemic viral infections, including hepatitis B virus (HBV), hepatitis C virus (HCV), and human immunodeficiency virus (HIV).

Anti-inflammatory agents can be incorporated into BNPs or NNPs for the prevention and/or of treatment of inflammatory skin diseases, including Atopic dermatitis, Allergic contact dermatitis (poison ivy), Psoriasis, Dermatitis NOS, cutaneous lupus erythematosus, vitiligo, and alopecia areata.

8. Use in Follicular and Cutaneous Diseases

Anti-acne agents can be incorporated into BNPs or NNPs for prevention and/or treatment of acne vulgaris, hydradenitis suppurative, folliculitis decalvans, and dissecting folliculitis. Exemplary agents include benzyol peroxide, retinoids, including tretinoin, and dapsone. Anti-acne agents can be incorporated into BNPs or NNPs for prevention and/or of treatment of acne vulgaris, hydradenitis suppurative, folliculitis decalvans, and dissecting folliculitis.

In other embodiments, topical formulations include NNPs and BNPs for the stimulation of hair growth to treat conditions that cause alopecia, including androgenetic alopecia, alopecia areata, traction alopecia, scarring alopecia, and lichen planopilaris. In addition, topical formulations may include BNPs for the temporary filling of hair defects ("bald spots" or "thinning hair") and for purposes of hair thickening by using BNPs with polymers that mimic hair appearance and texture. In other embodiments, topical formulations may contain NNPs and/or BNPs targeted to the hair follicles and pores and sweat glands for hyperhydrosis control, as antiperspirants, and/or deodorants.

Structural or enzymatic proteins can be incorporated into BNPs or NNPs for the treatment and/or prevention of cutaneous diseases, such as filaggrin for atopic dermatitis or ichthyosis vulgaris, transglutaminase for autosomal-recessive congenital ichthyosis (ARCI), collagen VII for dystrophic epidermolysis bullosa (DEB), keratin 5 and/or 14 for epidermolysis bullosa simplex (EBS), and keratin 1 and/or 10 for bullous congenital ichthyosiform erythroderma (BCIE).

9. Insect Repellants and Pesticides

Topical formulations with NNPs and/or BNPs incorporating insect, arthropod, arachnid repellents, and pesticides may be used in reduction or prevention of bites and stings (e.g. mosquitos, ticks, bedbugs, flies, lice), as well as vector transmission of percutaneously introduced diseases. Such diseases include malaria, Lyme disease, leismaniasis, lice outbreaks and Chagas disease. Examples of agents incorporated into NNPs and/or BNPs for this use include DEET, natural or essential oil insect repellents, e.g. citronella oil, Neem oil, birch tar, bog myrtle, and permethrin. High concentration and/or stronger repellents and pesticides may be made safer by BNPs for use on skin, e.g. for military operations, desert and/or rain forest applications.

10. Cancer

NNPs and BNPs can also be formulated with chemotherapeutic agents and other pharmacological agents for the treatment of cancer. Therapeutically effective amounts of the disclosed particles used in the treatment of cancer will generally kill tumor cells or inhibit proliferation or metastasis of the tumor cells. Symptoms of cancer may be physical, such as tumor burden, or biological such as proliferation of cancer cells. The actual effective amounts of particles can vary according to factors including the specific particles administered, the particular composition formulated, the mode of administration, and the age, weight, condition of the subject being treated, as well as the route of administration and the disease or disorder. In exemplary embodiments, the particles are administered in an amount effective to kill cancer cells, improve survival of a subject with cancer, or a combination thereof. The cancer can be a skin cancer. In particular embodiments the strategy is utilized to target treat a cutaneous tumor type, such as malignant (melanoma, squamous cell carcinoma, basal cell carcinoma, merkel cell carcinoma, dermatofibroma sarcoma protuberans, cutaneous T cell lymphoma, cutaneous B cell lymphoma) premalignant (actinic keratoses, dysplastic nevi), photodamaged or aging skin changes (lentigos, rhytides), and benign neoplasms (dermatofibromas, lipomas, seborrheic keratoses).

Anti-cancer agents/active pharmacologic ingredients APIs incorporated into BNPs and NNPs may be (1) directly toxic to tumor cells, as in chemotherapeutic agents generally, (2) immune modifying, as in TLR agonists like imiquimod, and/or (3) inhibitors (cytokines, toxins, or other APIs) of tumor associated macrophages (TAMs) that are known to decrease anti-tumor immunity.

Representative anti-cancer agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel, epothilones A-F, and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), and combinations thereof. Other suitable anti-cancer agents include angiogenesis inhibitors including antibodies to vascular endothelial growth factor (VEGF) such as bevacizumab (AVASTIN®), other anti-VEGF compounds; thalidomide (THALOMID®) and derivatives thereof such as lenalidomide (REVLIMID®); endostatin; angiostatin; receptor tyrosine kinase (RTIC) inhibitors such as sunitinib (SUTENT®rosine kinase inhibitors such as sorafenib (Nexavar®), erlotinib (Tarceva®), pazopanib, axitinib, and lapatinib; transforming growth factor-α or transforming growth factor-β inhibitors, and antibodies to the epidermal growth factor receptor such as panitumumab (VECTIBIX®), and cetuximab (ERBITUX®), and newer generation immunotherapy drugs such as Ipilimumab, nivolumab.

An effective amount of the particles can be compared to a control. Suitable controls are known in the art. A typical control can be a comparison of a condition or symptom of a subject prior to and after administration of the particles, or a comparison between one particle and another or drug in a particle compared to free drug.

In the Examples below, BNP-DiO particles showed markedly enhanced depot, localization (around), and uptake (within) by the melanoma tumor cells, relative to the control NNP-DiO particles. The results indicate that BNP enhances delivery to cutaneous neoplasms. Thus in particularly preferred embodiments, BNPs are loaded with an anti-cancer agent and show improved cancer treatment compared to NNPs loaded with the drug.

The present invention will be further understood in view of the following non-limiting examples.

EXAMPLES

Example 1

Preparation of HPG Coated Particles

Materials and Methods

Polylactic acid (Mw=20.2 kDa, Mn=12.4 kDa) was obtained from Lactel.

$H_2N$-PEG(5000)-$OCH_3$ was obtained from Laysan.

Anhydrous dimethylformide, dichloromethane, diisopropylcarboimide, dimethylaminopyridie, potassium methoxide, camptothecin, polyvinyl alcohol, paraformaldehyde, TWEEN® 80, and 1,1,1-trihydroxymethyl propane were obtained from the Sigma-Aldrich.

Anhydrous dry ether, methanol, acetonitrile and dimethylsulfoxide were obtained from J. T. Baker.

1,1'-Dioctadecyl-3,3,3',3'-Tetramethylindodicarbocyanine,4 Chlorobenzenesulfonate Salt (DiD) was obtained from Invitrogen.

Super frost microscope slides were obtained from Thermo Scientific.

Microdialysis tubing was from Thermo Scientific.

IR-780 iodide, hydroxylamine solution (50%), glycerol, polyvinyl alcohol, $NaIO_4$ and bovine serum albumin (BSA) were obtained from the Sigma-Aldrich.

The 1,1'-Dioctadecyl-3,3,3',3'-Tetramethylindodicarbocyanine,4 Chlorobenzenesulfonate Salt (DiD) and DAPI stain were ordered from Invitrogen.

Donkey normal serum and Rabbit-anti-CD31 antibody was provided by Abcam and the Donkey-anti-rabbit secondary antibody tagged with Alexa488 fluorophore was from Invitrogen.

Aldehyde Quantification Assay Kit (Fluorometric) and were from Abcam.

Sunscreen lotion (SPF 30) was purchased from Walgreens.

Sunscreen oil (SPF 30) was from L'Oréal Paris.

Synthesis of Hyperbranched Polyglycerol

Hyperbranched polyglycerol (HPG) was synthesized by anionic polymerization. Briefly, 4.6 mmol 1,1,1-trihydroxypropane (THP) was added into an argon protected flask in a 95° C. oil bath and 1.5 mmol $KOCH_3$ was added. The system was hooked up to a vacuum pump and left under vacuum for 30 min. The system was refilled with argon and 25 ml glycidol was added by a syringe pump over 12 hours. The HPG was dissolved in methanol and precipitated by addition of acetone. HPG was purified 2-3 times with methanol/acetone precipitation. To further remove the low molecular weight HPG, 2-5 ml HPG was placed in a 10 ml dialysis tube (0.5-1 k cut-off) and dialyzed against deionized (DI) water. The water was replaced two times every 12 hours. HPG was precipitated with acetone and then dried under vacuum at 80° C. for 12 h.

Synthesis of PLA-HPG and PLA-PEG Copolymers

PLA (5 g) and 2.15 g HPG were dissolved in dimethyl formamide (DMF) and dried over molecular sieves overnight. 0.06 ml diisopropylcarboimide (DIC) and 10 mg 4-(N,N-dimethylamino)pyridine (DMAP) were added and the reaction proceeded for 5 days at room temperature under stirring. The product was precipitated by pouring the reaction into cold diethyl ether (ether) and collecting the precipitate by centrifugation. The product was redissolved in dichloromethane (DCM) and precipitated again with a cold mixture of ether and methanol. The product was washed with a cold mixture of ether and methanol. The polymer was dried under vacuum for 2 days.

To synthesize PLA-PEG, 2.6 g PLA and 1.0 g MPEG-$NH_2$ were dissolved in DMF and dried over molecular sieves overnight. 0.038 ml DIC was added and the reaction proceeded for 2 days at room temperature under stirring. The product was precipitated by pouring the reaction into cold ether and collecting the precipitate by centrifugation. The product was redissolved in DCM and precipitated again with cold ether, washed with a cold mixture of ether and methanol and dried under vacuum for 2 days.

Fabrication of Nanoparticles (NPs)

Fifty mg of PLA-HPG copolymer dissolved in 1.5-3.0 ml of ethyl acetate/dimethyl sulfoxide (DMSO) (4:1) was added to 4 ml DI water under vortexing and subjected to probe sonication for 3 cycles at 10 sec each. The resulting emulsion was diluted in 20 ml DI water under stirring. It was stirred for at least 5 hours or attached to a ratovapor to evaporate the ethyl acetate and then applied to an Amico ultra centrifuge filtration unit (100 k cut-off). The NPs were washed by filtration 2 times then suspended in a 10% sucrose solution. The NPs were kept frozen at −20° C.

The PLA-PEG NPs were made using a single emulsion technique. 50 mg PLA-PEG copolymer dissolved in 1.5-3.0 ml ethyl acetate/DMSO (4:1) was added to 4 ml DI water with 2.5% PVA under vortexing and subjected to probe sonication for 3 cycles of 10 sec each. The resulting emulsion was diluted in 20 ml DI water with 0.1% Tween® 80 with stirring. The emulsion was stirred for at least 5 hours or attached to a ratovapor to evaporate the ethyl acetate and then the solution was applied to an Amico ultra centrifuge filtration unit (100 k cut-off). The NPs were washed by filtration for 2 times then suspended in a 10% sucrose solution.

Characterization of Nanoparticles (NPs) by Transmission Electron Microscopy (TEM).

The NPs were characterized with TEM. A drop of nanoparticle suspension was applied on the top of carbon coated copper grids and most of the droplet was removed with a piece of filter paper. The thin layer of NPs suspension was dried for 5-10 min and then a droplet of uranyl acetate was applied. Most of the droplet was removed with a filter paper and left to dry for 5 min. The sample was mounted for imaging with TEM. The size distribution of NPs was analyzed in Image J. The hydrodynamic size of NPs was determined by dynamic laser scattering (DLS). NPs suspension was diluted with DI water to 0.05 mg/ml and 1 ml was loaded into the cell for detection.

To determine the concentration of the dye in NPs, 990 μL DMSO was added to 10 μL NPs in aqueous solution. The solution was vortexed and left in the dark for 10 min. The concentration of the dye was quantified with a plate reader by fluorescence of the DiD dye at 670 nm with an excitation wavelength at 644 nm.

Results $^1$H NMR spectra for HPG and PLA-HPG block-copolymer were recorded on a 400 MHz Agilent instrument using DMSO-d6 as solvent. Inverse gated $^{13}$C NMR spectra for HPG were recorded on a 600 MHz Agilent instrument with methanol-d4 as solvent.

The $\overline{DP_n}$ (number-average degree of polymerization) for HPG was calculated according to the inverse gated $^{13}$C NMR spectra for HPG with the following equation:

$$\overline{DP_n} = \frac{(T + L_{13} + L_{14} + D)}{(T - D)} f_c$$

The functionality of the core molecule (TMP), $f_c$, is 3.
The Mn of HPG is calculated with the following equation:

$Mn$=Molecular weight of glycidol×$\overline{DP_n}$ of HPG+ molecular weight of TMP.

Both particles have a biodegradable PLA core, which can be used to load hydrophobic agents, and a hydrophilic shell of HPG or PEG. HPG was made by anionic polymerization and characterized by $^1$H NMR and $^{13}$C NMR. PLA-HPG copolymer was synthesized by esterification and the conjugation of PLA-HPG was confirmed by $^1$H NMR. The weight percentage of HPG in PLA-HPG was about 29% as calculated from the NMR results.

PLA-HPG NPs were made from a single emulsion as described above. PLA-PEG copolymer was synthesized by the conjugation of PLA-COOH with amine terminated mPEG and also characterized with $^1$H NMR. The weight percentage of PEG was about 26% as calculated from the NMR results. Transmission electronic microscopy (TEM) confirmed the spherical shape of the PLA-HPG and PLA-PEG NPs. The hydrodynamic diameter of NPs was 100 nm as measured by dynamic light scattering (DLS) (Table 1).

TABLE 1

Average diameter of PLA-HPG nanoparticles and PLA-PEG nanoparticles.

| NPs | Diameter (nm) |
|---|---|
| PLA-HPG | 102.1 ± 3.1 |
| PLA-PEG | 103.3 ± 1.0 |

Example 2

Evaluation of NPs In Vitro

Materials and Methods

Microdialysis tubes were filled with 100 μL of NPs loaded with 1,1'-dioctadecyl-3,3,3',3'-tetramethylindodicarbocyanine, 4-chlorobenzenesulfonate Salt (DiD) and placed on a floater in a large beaker with 4 L PBS at 37° C. Tubes were removed in triplicates at different time points. The PBS was changed every 12 hours. The dye left in the dialysis tube was quantified by fluorescence.

Results

Figure 2:
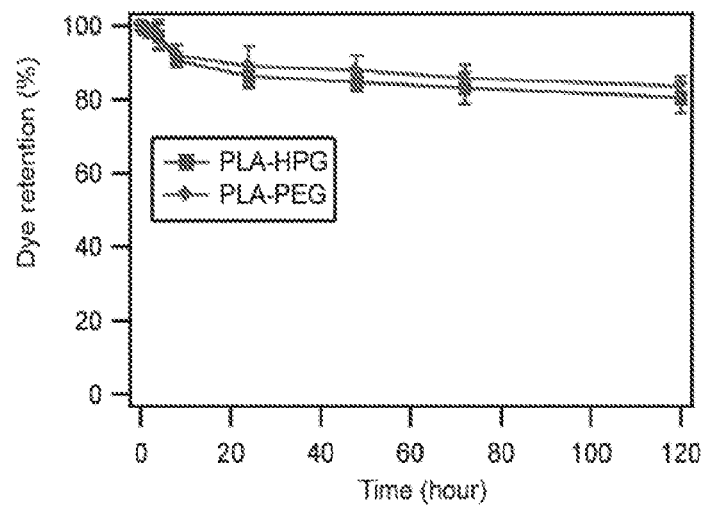
FIG. 2 is a graph showing dye retention (%) of PLA-HPG and PLA-PEG nanoparticles as a function of incubation time in PBS.

DiD-loaded NPs release a minimal amount of dye (~20%) over 5 days of continuous incubation in PBS (FIG. 2). Both PLA-HPG and PLA-PEG NPs were loaded with equivalent amounts of DiD.

Example 3

Evaluation of Reversibility of Stealth Properties of Nanoparticles in Blood Circulation Materials and Methods Synthesis of Functionalized HPG-Coated Nanoparticles.

PLA-HPG NPs (0.1 mg/ml) in a 96-well plate (small vial) were incubated with 1 mM NaIO$_4$ and at each time point, the reactions were quenched with 2 mM Na$_2$SO$_3$. The NPs were washed two times with DI water in an AcroPrep filter plate with 100 k cut-off (or amicon ultra filter 0.5 ml with 100 k cut-off) and then suspended in DI water.

The aldehydes on NPs were quantified with an aldehyde quantification assay kit (Abeam). The PLA-HPG NPs were used as a background subtraction control. The amount of aldehyde was calculated by comparing to a reference curve. The reference curve was made by using the aldehyde standard provided with the kit. The amount of aldehyde on each particle was calculated based on 100 nm hydrodynamic diameter of NPs and an assumed NP density of 1.0 g/cm$^3$. For microarray printing, NPs load with DiD dye were suspended in PBS buffer containing 15% glycerol and 0.01% triton-X100 at a concentration of 1 mg/ml in a 384-well plate. The NPs were arrayed on lysine coated slides using a Spotbot microrrayer from Arrayit. After 1 hour incubation in a humidity chamber, the printed slides were washed extensively with PBS 3 times, 5 min each. After a quick rinse with DI water, the slides were blow-dried with argon and subjected for imaging.

For ligand or protein attachment, in a 96-well plate (or small vials), PLA-HPG$_{ALD}$ NPs were incubated with ligands or proteins (NaCNBH$_4$ should be added for proteins or ligands modified with amines or hydrazines) for 1 min-12 hours and the reaction was quenched with an excess amount of hydroxylamine (or ethanolamine for proteins or ligands modified with amines or hydrazines) solution in TRIS buffer (PH=7.4). The NPs were transferred to an AcroPrep filter plate with 100 k cut-off (or amicon ultra filter 0.5 ml with 100 k cut-off or gel filtration for proteins and other large molecules) and washed two times with DI water or buffer.

Modification of HPG Surface Properties

To reduce the PLA-HPG$_{ALD}$ NPs (sticky, also referred to herein as bioadhesive nanoparticles, BNPs) back to PLA-HPG NPs (also referred to herein as non-bioadhesive nanoparticles, NNPs), PLA-HPG$_{ALD}$ NPs were incubated with NaBH$_4$ in NaH$_2$PO$_4$ (0.2M, PH=8.0) and the reaction was quenched with acetic acid and neutralized with PBS buffer. The NPs were washed with DI water twice. The blood circulation experiments were performed to test the stealth properties of the nanoparticles.

Results

PLA-HPG$_{ALD}$ NPs (BNPs) could be reversed to PLA-HPG$_{Reversed}$ (stealth) NPs by NaBH$_4$ treatment, though one alcohol group is lost with the reduction-reversal cycle since each vicinal diol on HPG is oxidized by NaIO$_4$ to an aldehyde and each aldehyde is reduced to a single alcohol by NaBH$_4$. The blood circulation confirmed that the PLA-HPG$_{ALD}$ NPs lost almost all their stickiness after treatment with NaBH$_4$. The back and forth tunability also demonstrated the robustness of the HPG coating on the nanoparticles.

Example 4

Evaluation of Adherence of Functionalized NPs

Materials and Methods

Polylysine coated glass slides were used as a tissue mimic to evaluate the bioadhesive property of PLA-HPG$_{ALD}$ NPs (BNPs). PLA-HPG$_{ALD}$ NPs with different concentrations of aldehydes were prepared using a high-throughput procedure, where regular 96-well plates and 96-well filter plates were used to prepare the NPs and printed onto polylysine coated slides with a microarrayer. The PLA-HPG NPs (NNPs) without NaIO$_4$ treatment did not adhere to glass slides and only background signal was detected. However, by transforming the surface property with NaIO$_4$, the amount of NPs immobilized on the glass slide increased as a function of duration of NaIO$_4$ treatment, indicating that the bioadhesive property of the PLA-HPG NPs can be tuned by control of NaIO$_4$ treatment.

For microarray printing, NPs load with DiD dye were suspended in PBS buffer containing 15% glycerol and 0.01% TRITON®-X100 at a concentration of 1 mg/ml in a 384-well plate. The NPs were arrayed on lysine coated slides using a SPOTBOT® microrrayer from ARRAYIT®. After 1 hour incubation in a humidity chamber, the printed slides were washed extensively with PBS 3 times, 5 min each. After a quick rinse with DI water, the slides were blow-dried with argon and subjected for imaging The bioadhesive property of PLA-HPG NPs on tissues was evaluated by applying suspended NPs ex vivo to the external surface of pig skin. Fresh pig skin was obtained from a local slaughterhouse and the hair was carefully removed by a trimmer, making sure no damage occurred to the skin. The skin was frozen at −20° C. The skin was thawed on ice before use. Thawed pig skin was washed with PBS buffer and cut to 2×2 cm pieces. DiD-loaded PLA-HPG NPs (NNPs) and PLA-HPG$_{ALD}$ NPs (BNPs) in PBS were topically applied to pig skin and incubated for 6 h in a humidity chamber at 32° C. After incubation, skin was washed with plenty of PBS buffer and frozen in OCT. The frozen skin was sectioned into 10-20 μm slices, mounted on glass slides, and imaged with an EVOS fluorescence microscope.

For the live imaging study of adherence of PLA-HPG$_{ALD}$ NPs to the skin on Nude mice, the dorsal skin of each Nude mouse was cleaned with an alcohol pad and 1 mg/ml of IR-780/PLA-HPG$_{ALD}$ NPs (0.5%) in PBS was applied to the skin. The nanoparticles remaining on the skin were imaged by XENOGEN®. The mice were housed individually and imaged at each time point. For evaluation of PLA-HPG$_{ALD}$ NPs water resistance and mechanical removal, one group of Nude mice (n=3) was wiped with a wet towel and the other group of mice was washed with water. The mice were subsequently dried with kimwipes and sent for live imaging.

Results

Figure 3A:
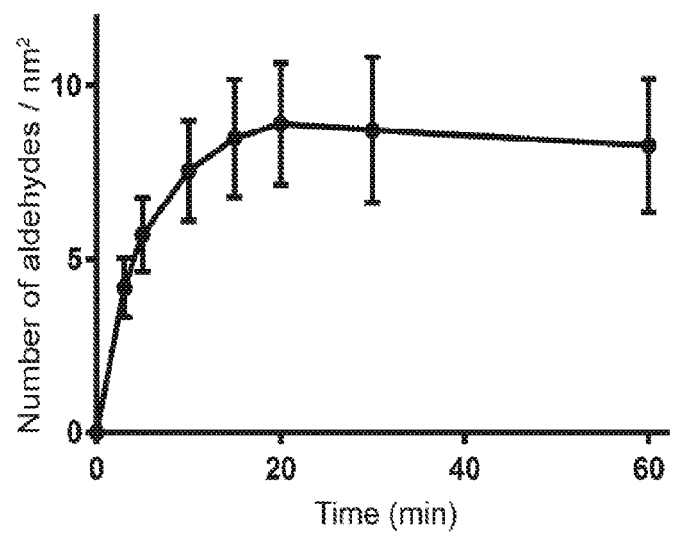
FIG. 3A is a graph showing the number of aldehyde groups/nm$^2$ on stealth NPs as a function of incubation time with NaIO$_4$. Data are shown as mean±SD (n=4).
Figure 3B:
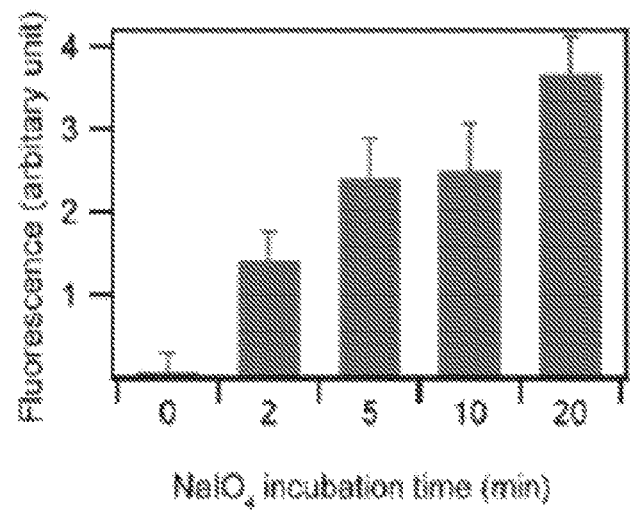
FIG. 3B is a graph showing surface immobilization of DiD loaded PLA-HPG NPs treated with NaIO$_4$ for different periods of time (min) on lysine coated slides. Data are shown as mean±SD (n=4).
Figure 3C:
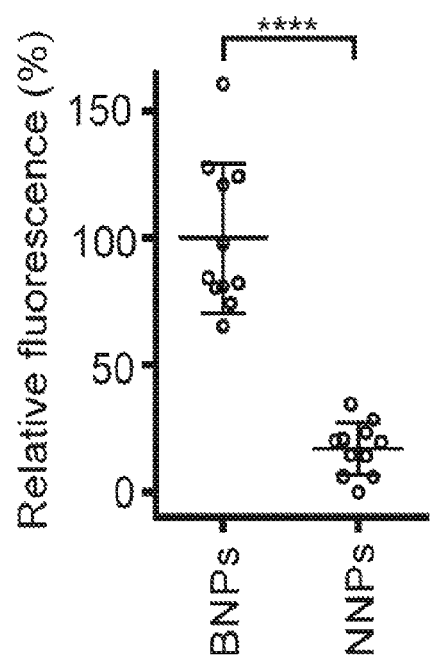
FIG. 3C is a graph of relative fluorescence (%) obtained from sections of pig skin incubated with DiD-loaded PLA-HPG$_{ALD}$ NPs (bioadhesive nanoparticles, BNPs) and DiD-loaded PLA-HPG NPs (non-bioadhesive nanoparticles, NNPs) at 1 mg/ml for 6 hours in a humidity chamber at 32° C. The fluorescence was quantified and normalized to the average fluorescence of the PLA-HPG$_{ALD}$ on pig skin. Data are shown as mean±SD (n=10).

The results are shown in FIGS. 3A-3C. PLA-HPG$_{ALD}$ NPs showed greater retention on pig skin than PLA-HPG NPs (P<0.05). The fluorescence intensity was quantified from the fluorescence images.

Because the HPG coating is rich in vicinal diols, PLA-HPG NPs can be readily oxidized to aldehyde-terminated PLA-HPG$_{ALD}$ NPs by sodium periodate (NaIO4) treatment. This was validated by H$^1$NMR and Schiff's agent analysis. The surface density of aldehydes on PLA-HPG$_{ALD}$ NPs was monitored as a function of incubation time with NaIO$_4$ and it reached its saturation at about 20 min (FIG. 3A). The final surface density of aldehydes on PLA-HPG$_{ALD}$ NPs approached 9/nm$^2$ (17 aldehydes/PLA molecule), indicating that the majority of surface vicinal diols were converted to aldehydes. This surface density of functional groups is at least one order of magnitude higher than previously reported on biodegradable NPs (Gu et al., *Proc. Natl. Acad. Sci. U.S.A.* 105:2586-2591 (2008)). Moreover, the surface density of the aldehydes can be controlled by incubation time with NaIO$_4$. No detrimental effects of aldehyde conversion were observed on NPs by TEM imaging. The average diameter of NPs was approximately 96 nm by dynamic light scattering (DLS) measurement (Table 2).

The bioadhesive properties of the PLA-HPG$_{ALD}$ NPs (BNPs) using polylysine coated glass slides as a tissue mimic (Rao et al., *J. Biomater. Sci. Polym. Ed.* 22:611-625 (2011)) was investigated. PLA-HPG$_{ALD}$ NPs (BNPs) with different concentrations of aldehyde were prepared and printed onto polylysine coated slides with a microarrayer. PLA-HPG NPs (NNPs) did not adhere to glass slides (FIG. 3B). However, after oxidizing surface HPG vicinal diols into aldehydes with NaIO$_4$, the amount of PLA-HPG$_{ALD}$ NPs immobilized on the glass slide increased as a function of NaIO$_4$ treatment duration (FIG. 3B), indicating that the bioadhesive property of the PLA-HPG$_{ALD}$ NPs increases with a longer duration of NaIO$_4$ treatment. Moreover, the large capacity for surface aldehyde modification allows for tuning adhesiveness for specific topical applications.

TABLE 2

Diameter (nm) and polydispersity index (PDI) of various nanoparticies.

| Nanoparticies (NPs) | Diameter (nm) | PDI |
|---|---|---|
| PLA-HPG$_{ALD}$ | 96 | 0.273 |
| DiD/PLA-HPG | 120 | 0.211 |
| DiD/PLA-HPG$_{ALD}$ | 118 | 0.232 |
| IR-780/ PLA-HPG$_{ALD}$ | 128 | 0.334 |
| PO/PLA-HPG$_{ALD}$ | 138 | 0.227 |

Delivery vehicles for UV-filters should ideally remain only on the skin surface, without penetration into the epidermis, dermis, or hair follicles, in order to avoid potential health risks (Krause, et al., *Int. J. Androl.* 35:424-436 (2012)). Thus, the retention and the penetration of PLA-HPG$_{ALD}$ NPs ex vivo to PLA-HPG NPs by applying suspended particles topically onto pig skin was compared. To facilitate imaging and quantification, both NPs were loaded with a hydrophobic dye, 0.2% 1,1'-dioctadecyl-3,3,3',3'-tetramethylindodicarbocyanine,4-chlorobenzenesulfonate salt (DiD) (Deng et al., *Biomaterials.* 35:6595-6602 (2014)). Both the DiD/PLA-HPG NPs and DiD/PLA-HPG$_{ALD}$ NPs were characterized by TEM and DLS (Table 2), and had a similar spherical morphology. After incubation for 6 hours with both NPs, followed by extensive washing, PLA-HPG$_{ALD}$ NPs showed substantially higher retention on pig skin compared to NNPs (FIG. 3C). No penetration of PLA-HPG$_{ALD}$ NPs was observed on any pig skin samples; however, PLA-HPG NPs penetrated into the pig skin follicles without significant retention on the stratum corneum. Pig skin is considered a good mimic for human skin in a variety of applications including penetration studies for chemicals and nanoparticles (Swindle et al., *Veterinary Pathology* 49:738-738 and 344 (2012); Barbero et al., *Toxicol. In Vitro*

23:1-13 (2009)). These results indicate that PLA-HPG$_{ALD}$ NPs exhibit no skin penetration whereas the PLA-HPG NPs exhibit considerable penetration into follicles, reflect the adhesion of PLA-HPG$_{ALD}$ NPs to proteins on the skin surface, which prevents diffusion of nanoparticles to deeper skin layer or into follicles.

Figure 4A:
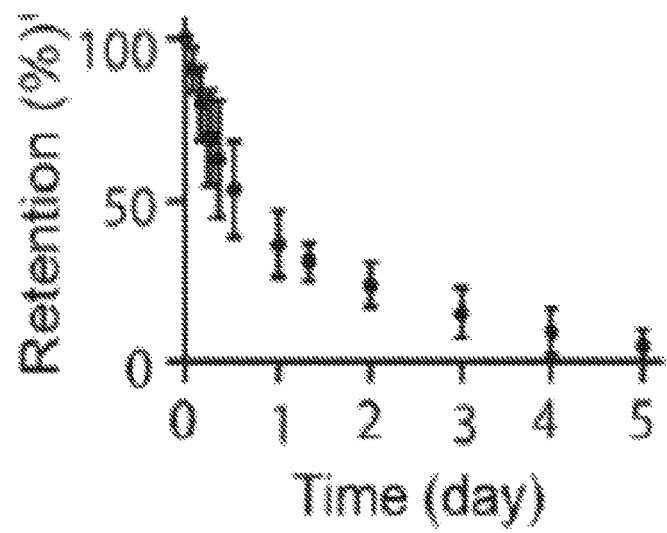
FIG. 4A is a graph showing percent retention (%) of PLA-HPG$_{ALD}$ NPs encapsulating an infrared dye, IR-780, as a function of time (days) following application to the dorsal skin of mice.
Figure 4B:
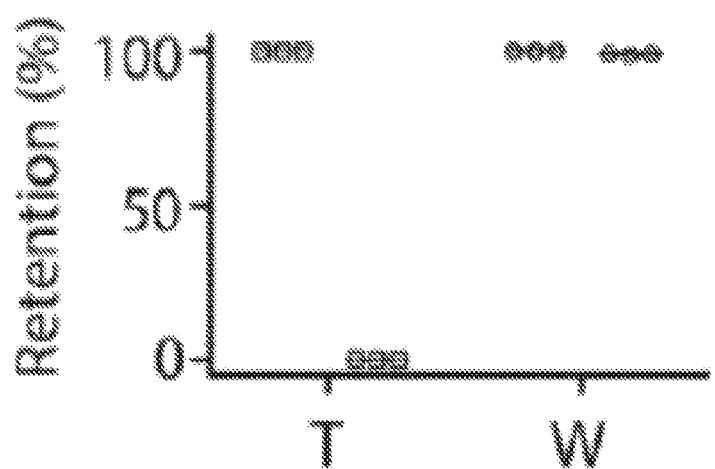
FIG. 4B is a graph showing percent retention (%) of PLA-HPG$_{ALD}$ NPs encapsulating an infrared dye, IR-780, as a function of treatment with towel (T) or water (W). After washing with water or wiping with a wet towel, the PLA-HPG$_{ALD}$ NPs skin retention was imaged with Xenogen. The fluorescence was quantified and normalized to the fluorescence intensity at the starting point.

The water resistance and potential for removal of PLA-HPG$_{ALD}$ NPs by encapsulating an infrared dye, IR-780, into BNPs (0.5% loading), and measuring nanoparticle skin concentrations with in vivo imaging was investigated. The IR-780/PLA-HPG$_{ALD}$ NPs were characterized by TEM and DLS (Table 2). After extensive washing with water, no significant change in fluorescence was observed; however, the PLA-HPG$_{ALD}$ NPs were removed after wiping with a wet towel (FIGS. 4A and 4B). If untreated, PLA-HPG$_{ALD}$ NPs concentration diminished markedly (approximately 75%) within 24 hr and disappearance was essentially complete after five days (FIG. 5A).

These examples show that PLA-HPG$_{ALD}$ NPs will interact with tissues since the bioadhesive property of PLA-HPG$_{ALD}$ NPs is resulted from the Schiff-base bond between the aldehyde groups on PLA-HPG$_{ALD}$ NPs and the amine groups in tissue surface.

These results support the use of PLA-HPG NPs in local delivery where an extended retention at delivery sites is needed. The density of the aldehydes on NPs can be controlled thereby providing tunability in the behavior of the PLA-HPG$_{ALD}$ NPs for local delivery, especially since the PLA-HPG NPs penetrated into hair follicles on the pig skin.

Sunscreens based on PLA-HPG$_{ALD}$ NPs can simplify the current sunscreen formulation as well as eliminate the use of irritants and/or allergens. PLA-HPG$_{ALD}$ NPs are ideal vehicles for sunscreen application since they are water-soluble but their interaction with skin is water-resistant. The PLA-HPG$_{ALD}$ NPs disappear from skin naturally by exfoliation of the stratum corneum; removal can be accelerated mechanically by towel drying. Moreover, nanoparticles, of the size used in this study, yield more transparent suspensions, which may be favored in topical applications for aesthetic reasons.

Example 5

Synthesis of Padimate O (PO)-loaded PLA-HPG$_{ALD}$ NPs

Materials and Methods

PLA-HPG polymer and PO (an organic compound used in sunscreens), in certain ratio (ratio from 1:1 to 20:1 and total mass of 50-100 mg), were dissolved in 1.5-3.0 ml solvent mixture (Ethyl acetate:DMSO=4:1) was added into 4 ml DI water under vortexing and then subjected to probe sonication for 3 cycles at 10 sec each. The resulting emulsion was diluted in 20 ml DI water with stirring. It was hooked up to a rotovapor to evaporate the ethyl acetate and then applied to an Amico ultra centrifuge filtration unit (100 k cut-off). The PO/PLA-HPG NPs were washed by filtration 2 times then suspended in DI water. The same procedure was implemented to produce PLA-HPG$_{ALD}$ NPs, as PO/PLA-HPG$_{ALD}$ NPs can be oxidized from PO/PLA-HPG NPs nanoparticles.

To quantify the PO loading, the nanoparticles were dissolved in DMSO and the UV absorbance at 310 nm was measured with a plate reader. The amount of PO was calculated by comparing to a reference curve.

Results

All PO/PLA-HPG$_{ALD}$ NPs contained 10% PO. The spherical shape of the PO/BNPs was confirmed by TEM. A hydrodynamic diameter of 138 nm for PO/PLA-HPG$_{ALD}$ NPs was measured by DLS. The results for hydrodynamic diameter of all the NPs generated in these studies are presented in Table 2.

Example 6

PO-Loaded PLA-HPG$_{ALD}$ NPs Retain PO Under Conditions Mimicking Human Sweat The stability of PO encapsulation in NPs was evaluated by measuring the release of PO in buffer mimicking the pH range (4.5-7.4) of human sweat.

Materials and Methods

To quantify PO release from PLA-HPG$_{ALD}$ NPs, a suspension of 1 mg NPs loaded with PO in a dialysis tube (10K cut-off) was dialyzed against 40 ml PBS with 0.1% SDS at 32° C. At each time point, 150 µL solution was removed and 150 µL PBS with 0.1% SDS was added. The amount of released PO was quantified by UV adsorption at 310 nm with a plate reader.

Results

Figure 5:
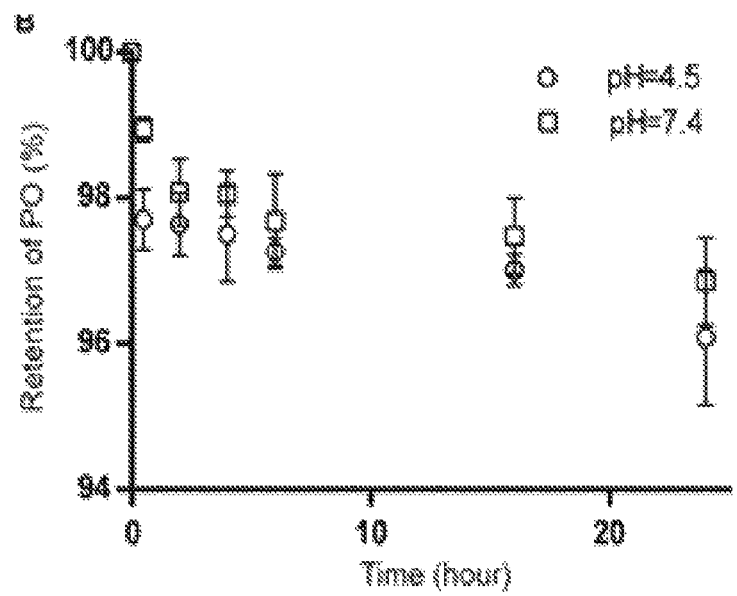
FIG. 5 is a graph showing percent retention of padimate O (PO) (%) within PO/PLA-HPG$_{ALD}$ NPs in releasing medium (containing 0.1% SDS) mimicking the pH range of human sweat as a function of time (hours). Data are shown as mean±SD (n=4).

The results are shown in FIG. 5. Under conditions mimicking the pH range of human sweat (4.5 and 7.4), PLA-HPG$_{ALD}$ NPs loaded with PO retained more than about 96% of the PO after 20 hours. The particles also exhibited UV absorption compared to PO dispersed in water or aqueous buffer.

Example 7

PO-Loaded PLA-HPG$_{ALD}$ NPs Effectively Absorb UV Light and and Confine Reactive Oxygen Species Most organic UV filters prevent sunburn by absorbing UV radiation. Therefore, their effectiveness can be estimated by measuring their UV absorption efficiency. Photoinduced changes in UV filters often produce toxic intermediates including ROS that are destructive to multiple cellular components including gDNA (Hanson et al., *Free Radical Biology and Medicine*, 41:1205-1212 (2006)). It has been reported that encapsulating UV filters in polymeric nanoparticles improves filter photostability and delays photodegradation of the UV filters (Perugini et al., *International Journal of Pharmaceutics*, 246:37-45 (2002)). To test whether encapsulating UV-filters in PLA-HPG$_{ALD}$ NPs would in turn confine any generated ROS within the nanoparticles, thereby eliminating potential side-effects, the PO/PLA-HPG$_{ALD}$ NPs and PO suspension were mixed with DHR and exposed to UV. The UV absorption of PO/PLA-HPG$_{ALD}$ NPs was evaluated by measuring their absorption spectrum within the UV range (260-400 nm).

Materials and Methods

PO/PLA-HPG$_{ALD}$ NPs suspended in water, PO emulsified in water and PO dissolved in mineral oil at a PO concentration of 0.01 mg/ml were aliquoted into a UV transparent plate and scanned through the UV absorbance spectrum from 260-400 nm with a plate reader. Blank PLA-HPG$_{ALD}$ NPs, water and mineral oil were also scanned as background controls. The PO emulsion in water was made by probe sonication. For the DHR assay, PO/PLA-HPG$_{ALD}$ NPs, PLA-HPG$_{ALD}$ NPs, PO water emulsion at a PO concentration of 0.1 mg/ml was incubated with DHR in 96 well plate.

After exposing to UV-B (280-320 nm), plate fluorescence was read at Ex/Em 500/536 nm.

Dihydrarhodamine (DM), a widely used ROS probe (Hanson et al., *Free Radical Biology and Medicine*, 41:1205-1212 (2006)), was used to detect reactive radicals generated by PO after UV exposure. DHR was mixed with PO/PLA-HPG$_{ALD}$ NPs, emulsified PO, and PLA-HPG$_{ALD}$ NPs separately and exposed to UV. DHR in PBS was used as a control because it absorbs UV at 280-315 nm and becomes fluorescent.

Results

Figure 6A:
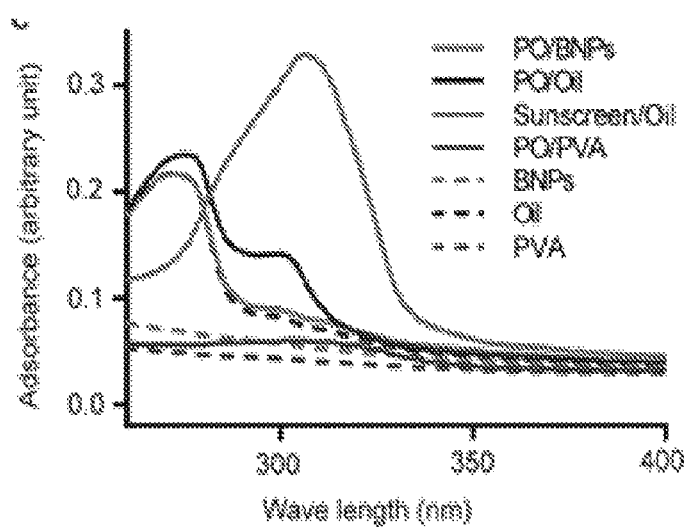
FIGS. 6A and 6B are graphs of 260-400 nm UV light absorbance by PO/PLA-HPG$_{ALD}$ NPs (PO/BNPs), PO emulsion in PVA solution (PO/PVA), PO dissolved in mineral oil (PO/Oil) at a PO concentration of 0.01 mg/ml, sunscreen dissolved in mineral oil (Sunscreen/Oil) at 0.01 mg/ml plotted without (FIG. 6A) and with (FIG. 6B) background subtraction of blank vehicles (BNPs, Oil and PVA). Data are shown as mean (n=4).
Figure 6B:
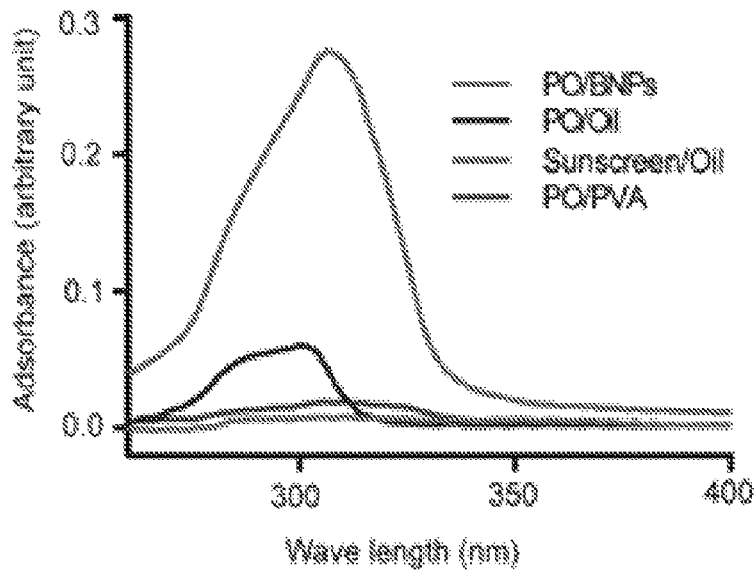

PO/PLA-HPG$_{ALD}$ NPs were compared to PO emulsified in polyvinyl alcohol (PVA) solution (PO/PVA), PO in mineral oil (PO/oil), sunscreen (L'Oreal sunscreen oil spray) in mineral oil (sunscreen/oil); blank PLA-HPG$_{ALD}$ NPs, mineral oil and PVA solution were used as controls (FIG. 6A). All solutions contained equivalent PO concentrations (0.01 mg/ml). PO/PLA-HPG$_{ALD}$ NPs showed a 20-fold higher absorption compared to the PO emulsion in PVA solution and sunscreen diluted in mineral oil (active ingredients adjusted to 0.01 mg/ml) after background subtraction of the appropriate base material (FIG. 6B).

The PO/PVA emulsion is a simplified, representative version of a sunscreen formulation (Allured, *Cosmet Toiletries*, 99:79-79 (1984)); most current sunscreens are based on an emulsion of UV filters (Tanner, *Dermatologic Clinics*, 24:53-62 (2006)). The sunscreen oil used in this example is an oil spray with the same active ingredients and SPF value as the sunscreen lotion used in the animal studies. These results indicate a significant improvement in UV absorption efficiency of PO/PLA-HPG$_{ALD}$ NPs compared to PO dissolved in mineral oil.

Figure 6C:
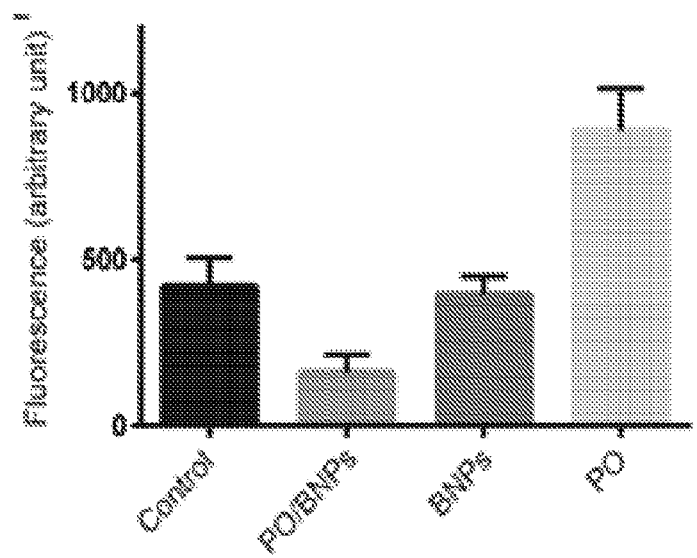
FIG. 6C is a graph showing fluorescence of DHR after DHR was mixed with PO/PLA-HPG$_{ALD}$ NPs (PO/BNPs), blank PLA-HPG$_{ALD}$ NPs (BNPs), PO emulsion (PO) and PBS control (Control) and exposed to UV. Data are shown as mean±SD (n=8). DHR—dihydrorhodamine, BNPs—bioadhesive nanoparticles (PLA-HPG$_{ALD}$ NPs), PO/BNPs—PLA-HPG$_{ALD}$ NPs encapsulating PO, PBS—phosphate buffered saline, PO—padamate O, PVA—polyvinyl alcohol.

The PLA-HPG$_{ALD}$ NPs had a negligible effect on the background fluorescence of DHR as measured by the control since they did not absorb UV. The fluorescence from the PO suspension is much higher than the control (FIG. 6C). It is believed that the free ROS generated from the photoactivated PO after UV exposure oxidized the DHR into fluorescent species. In contrast, by confining the ROS within NPs, the PO/PLA-HPG$_{ALD}$ NPs significantly decreased the background fluorescence.

Example 8

PO-Loaded PLA-HPG$_{ALD}$ NPs Protect Against Sunburn

The protective effect of the PO/PLA-HPG$_{ALD}$ NPs against sunburn on the dorsal skin of Nude mice was evaluated.

Materials and Methods

Nude mice were anesthetized with Ketamine/Xylazine, and their dorsal skin was cleaned with 70% alcohol and demarcated into four quadrants. One quadrant was used as a PBS control and other areas were treated with sunscreen, PO/PLA-HPG$_{ALD}$ NPs or blank PLA-HPG$_{ALD}$ NPs. Only the dorsal epidermis was exposed to the UV lamp (UV-A and UV-B, 280-400 nm, 8 W) for one min (2160 J/m$^2$) and the remaining skin was covered with screens. The mice were left in separate cages and monitored until they woke up. Three days after UV exposure, the dorsal skin was removed and prepared for histology. Images were analyzed for epidermal thickness and keratin content using ImageJ.

Results

Three days after UV exposure, skin treated with both PO/PLA-HPG$_{ALD}$ NPs and sunscreen contained no visible erythema, edema or ulceration. However, both skin patches treated with PBS and blank PLA-HPG$_{ALD}$ NPs were damaged considerably by the same UV exposure. A similar pattern of UV toxicity was seen after staining the dorsal skin with hematoxylin and eosin (H&E) (FIG. 7A). There was significant acanthosis with prominent rete ridges present in the unprotected samples, consistent with epidermal hypertrophy, whereas the skin protected by sunscreen or PO/PLA-HPG$_{ALD}$ NPs appeared comparable to normal controls. The UV filter (PO) concentration in PO/PLA-HPG$_{ALD}$ NPs was less than 5% of that contained in the sunscreen, yet the PO/PLA-HPG$_{ALD}$ NPs achieved a similar gross UV protection effect. Trichome staining was also employed to measure the anti-UV effect against sunburn (FIG. 7B). The skin protected by sunscreen showed thickened orthokeratosis, a more subtle epidermal response than to UV-damage, relative to the skin protected by PO/PLA-HPG$_{ALD}$ NPs and the normal skin control. Overproduction of keratin can cause keratosis pilaris, often blocking the opening of hair follicles and resulting in further skin irritation. These results may therefore also demonstrate another non-irritating benefit of sunblock based on PLA-HPG$_{ALD}$ NPs.

Example 9

PO-Loaded PLA-HPG$_{ALD}$ NPs Protect Against DNA Double-Stranded Breaks

The ability of the PO/PLA-HPG$_{ALD}$ NPs to protect against DNA double-stranded breaks (DSBs) was evaluated in FVB mice.

Materials and Methods

The dorsal hair of FVB mice was shaved with electric clippers and treated with depilatory cream. One week later, the mice received either PO/PLA-HPG$_{ALD}$ NPs, sunscreen, or no treatment followed by dorsal exposure to UV (160 J/m2) one hour after treatment. For cyclobutane pyrimidine dimers (CPDs) staining, dorsal skin flaps were removed five minutes after UV exposure, and incubated in PBS containing 20 mM EDTA for 2 hours at 37° C. to allow separation of the epidermis from the dermis. The epidermal sheet was then rinsed in PBS, fixed in acetone for 20 min at −20° C., then permeabilized in cold PBS containing 0.5% Triton X-100 for 30 min. Sheets were denatured with 0.4 M NaOH in 70% ethanol for 22 min and then washed with cold PBS containing 0.5% Triton X-100 four times, eight min each. Sheets were blocked with PBS containing 2% BSA, 0.5% Triton-X-100 and 1% goat serum for one hour at room temp, then stained overnight at 4° C. with anti-thymine dimer (2 mg/ml, Abcam #ab10347) and diluted in PBS containing 0.4% BSA and 0.5% Triton X-100.

The remaining steps were carried out at room temperature. Samples were washed in PBS containing 0.5% Triton-X 100 for two hour, stained for two hour with Alexa568-goat-anti-mouse IgG (Invitrogen), washed again, mounted in DAPI (Invitrogen) and examined under a Leica 5P Confocal microscope.

For γH2AX staining, 20 hours after UV exposure, dorsal skin flaps were removed and incubated in 0.5 M ammonium thiocyanate for 20 min at 37° C. to allow for separation of the epidermis from the dermis. The epidermal sheet was then rinsed in PBS, fixed in acetone for 20 min at −20° C., then rehydrated in cold PBS. Sheets were blocked and nuclei were permeabilized in PBS containing 2% BSA and 0.5% Triton-X-100 for one hour at room temp, then stained overnight at 4° C. with anti-γH2AX (1 mg/ml, clone JBW30, Millipore, Billerica, MA) and diluted in PBS containing 0.4% BSA and 0.5% Triton X-100.

The remaining steps were carried out at room temperature. Samples were washed in PBS containing 0.5% Triton-X 100 for two hour, stained for two hour with Alexa568-goat-anti-mouse IgG (Invitrogen), washed again, mounted in DAPI (Invitrogen) and examined under a Leica 5P Confocal microscope. For CPD staining, 5 fields/sheet (1 sheet/mouse) were taken using the stage control to move 1 mm between fields in a set pattern. The fluorescence from CPD staining on nuclei was quantified by image J. For γH2AX staining, all of the areas with γH2AX+ cells on a sheet (1 sheet/mouse) were imaged. The γH2AX+ cells were counted using ImageJ particle analyzer software with the threshold set to eliminate the very faint γH2AX staining. The surface concentration of γH2AX+ cells was calculated by dividing the overall number of the γH2AX+ cells on a sheet with the surface area of the sheet.

Results

Both PO/PLA-HPG$_{ALD}$ NPs and sunscreen showed no detectable CPDs, but the positive control (unprotected skin) revealed marked widespread CPD formation after UV exposure (FIG. 8). Even though UV filter content in PO/PLA-HPG$_{ALD}$ NPs was less than 5% of that in sunscreen, it achieved the same level of UV protection.

Figure 9:
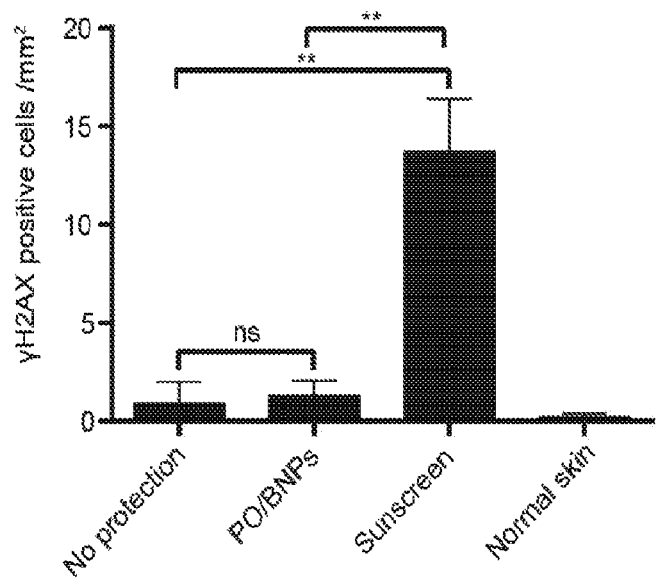
FIG. 9 is a bar graph of γH2AX positive cells per mm$^2$ in mouse dorsal skin sections that received different topical interventions. Skin sections were analyzed 20 hours after exposure to UV-B. The fluorescence of γH2AX on skin after each intervention was quantified. Data are shown as mean±SD (n=3), **p≤0.01 (student t-test). BNP—bioadhesive nanoparticles (PLA-HPG$_{ALD}$ NPs), γH2AX—phosphorylated histone H2AX, PO/BNP—bioadhesive nanoparticles (PLA-HPG$_{ALD}$ NPs) encapsulating PO, PO—padamate O.

DSBs induced by UV irradiation are highly carcinogenic. UVB exposure does not directly produce DSBs (Bastien et al., *The Journal of Investigative Dermatology*, 130:2463-2471 (2010)); however, it is possible that UV filters present in the epidermis and dermis can produce ROS after photoactivation, react with cellular DNA, and ultimately produce DSBs (Gulston and Knowland, *Mutat Res-Gen Tox En.* 444:49-60 (1999); Hanson et al., Free Radical Biology and Medicine, 41:1205-1212 (2006); Bastien et al., *The Journal of Investigative Dermatology*, 130:2463-2471 (2010); Girard et al., *J Phys Conf Ser.* 261 (2011); Limoli et al., *Proc. Natl. Acad. Sci. U.S.A.* 99:233-238 (2002); Han et al., *Cancer Res.* 64:3009-3013 (2004)). DSBs recruit phosphorylated histone H2A variant H2AX (γH2AX) to the damaged sites (Rogakou et al., *J. Biol. Chem.* 273:5858-5868 (1998)). The group of mice treated with conventional sunscreen showed the highest level of DNA-damage by γH2AX recruitment; in contrast, the level of γH2AX in both the PO/PLA-HPG$_{ALD}$ NPs and non-exposed control were comparable to the normal skin control (FIG. 9).

Summary

Figure 10A:
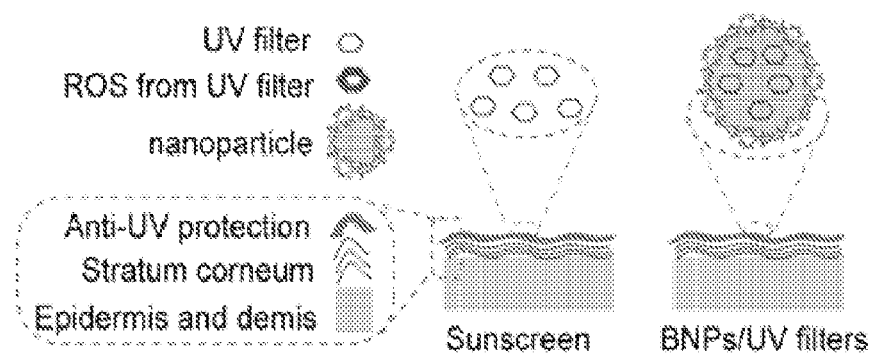
FIGS. 10A, 10B, and 10C are diagrams comparing application of commercial sunscreen (Sunscreen) to PLA-HPG$_{ALD}$ NP (BNPs)-based sunscreen (BNPs/UV filters).
Figure 10B:
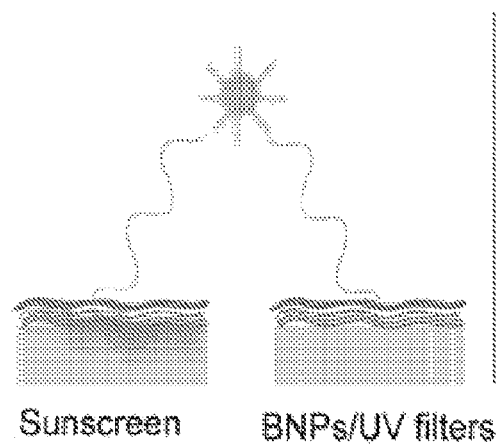
Figure 10C:
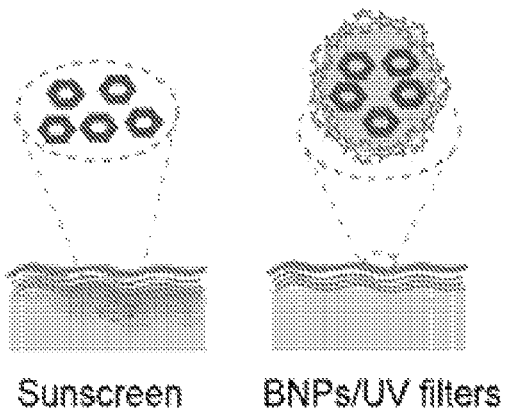

UV exposure from sunlight remains a significant health risk, and there continues to be controversy as to the safety and benefits of commercially available sunscreens. In order to address these issues, a sunblock based on PLA-HPG$_{ALD}$ NPs was developed. FIGS. 10A, 10B, and 10C are diagrams comparing application of commercial sunscreen (Sunscreen) to PLA-HPG$_{ALD}$ NP (BNPs)-based sunscreen (BNPs/UV filters). FIG. 10A is a diagram of sunscreen formulations applied onto the skin. FIG. 10B is a diagram of the skin after application: regular sunscreen penetrates into the skin whereas the PLA-HPG$_{ALD}$ NP (BNPs) formulation remains on the stratum corneum. FIG. 10C is a diagram of the skin after sunlight exposure: UV filters produce deleterious ROS, however, PLA-HPG$_{ALD}$ NPs (BNPs) do not penetrate into the skin and prevent ROS mediated toxicity by confining these toxic products within the particle.

Relative to conventional preparations, the PLA-HPG$_{ALD}$ NPs sunblock demonstrated a durable and specific adherence to the stratum corneum, without any evidence of penetration into cellular components of the epidermis (FIG. 10A); a 20-fold greater UV spectral absorbance; superior protection against UV-induced CPDs and DSBs (FIG. 10B); and protection against UV-induced orthokeraosis (FIG. 10C). Additionally, PLA-HPG$_{ALD}$ NPs on skin are water resistant, yet are easily removed with towel drying, or disappear naturally by exfoliation of the stratum corneum. Encapsulating UV filters within BNPs prevented skin exposure to the filter molecules, and the subsequent ROS produced after UV photochemical activation. With less than 5% UV filter encapsulation, the protective effect of PO/PLA-HPG$_{ALD}$ NPs against sunburn was comparable to commercial sunscreen in animal studies, and had the added benefit of preventing subsequent ROS mediated DSBs.

Example 10

BNP Augment Delivery of Anti-Cancer Agents/Active Pharmacologic Ingredients (APIs) to Cutaneous Tumors Materials and Methods DiD was incorporated at 2% concentration into the PLA core of BNPs and NNPs to assess the effects on depot, localization, and uptake by the tumor cells (DAPI, blue color) of established B16 melanoma tumors in C57BL/6 mice. BNPs and NNPs were injected with a 30-guage syringe into established B16 tumors in solvent 50:50 ethanol:cremaphor, at final concentration DiO 2.8 mg/ml. (bar, 50 μm).

Results

Major advantages of BNP encapsulation and delivery of chemotherapeutic and/or immune modifying agents to cutaneous tumors include: (1) the depot of anti-cancer agents/active pharmacologic ingredients (APIs) at the tumor site, with improved localization of API; (2) controlled release of API, with improved duration of release; (3) higher concentration of API within the tumor cells attributable to enhanced uptake by tumor cells of BNPs relative to NNPs.

An experiment was designed to assess the effects on depot, localization, and uptake of BNPs and NNPs by tumor cells. BNP-DiO particles showed markedly enhanced depot, localization (around), and uptake (within) by the melanoma tumor cells, relative to the control NNP-DiO particles. The results indicate that BNP enhances delivery to cutaneous neoplasms.

The same strategy can be utilized to target treat numerous cutaneous tumor types, including malignant (melanoma, squamous cell carcinoma, basal cell carcinoma, merkel cell carcinoma, dermatofibroma sarcoma protuberans, cutaneous T cell lymphoma, cutaneous B cell lymphoma) premalignant (actinic keratoses, dysplastic nevi), photodamaged or aging skin changes (lentigos, rhytides), and benign neoplasms (dermatofibromas, lipomas, seborrheic keratoses).

APIs incorporated into BNPs and NNPs may be (1) directly toxic to tumor cells, as in chemotherapeutic agents generally, (2) immune modifying, as in TLR agonists like imiquimod, or (3) inhibitors (cytokines, toxins, or other APIs) of tumor associated macrophages (TAMs) that are known to decrease anti-tumor immunity.

We claim:
1. A formulation for application to tissue, comprising particles comprising
   (i) a hydrophobic core,
   (ii) a shell, coating or corona comprising a hyperbranched polyglycerol not crosslinked with itself post-formation, wherein the hyperbranched polyglycerol is functionalized with an effective amount of one or more reactive functional groups exposed on the surface of the particles to adhere the particles to the tissue, wherein the hyperbranched polyglycerol is covalently bound to the hydrophobic core or polymers forming the core, wherein the one or more reactive functional groups are selected from the group consisting of aldehydes, amines, oximes, and O-substituted oximes, and (iii) one or more agents for application to the tissue, wherein the one or more agents are Janus kinase (JAK) inhibitors and/or signal transducer and activator of transcription (STAT) inhibitors, wherein the particles adhere to the tissue and/or release an effective amount of the one or more agents into the tissue for at least one day.

2. The formulation of claim 1, wherein the core comprises a hydrophobic polymer.

3. The formulation of claim 2, wherein the hydrophobic polymer is selected from the group consisting of poly(lactic acid), poly(glycolic acid), and copolymers thereof.

4. The formulation of claim 1, wherein the one or more reactive functional groups are aldehydes.

5. The formulation of claim 1, wherein the one or more agents are encapsulated within the particles.

6. The formulation of claim 1, wherein the average diameter of the particles is between about 1 nm and about 1 mm.

7. The formulation of claim 1, in a form selected from the group consisting of emulsions, lotions, creams, salves, irrigants, ointments, sprays, gels and foams.

8. The formulation of claim 1, wherein the amount or density of the one or more reactive functional groups is selected to control the degree of adherence of the particles to biological tissues, cells, or extracellular materials.

9. The formulation of claim 1, in the form of a skin repair or anti-aging formulation, hair product formulation, or combination thereof.

10. A method for delivering JAK inhibitors and/or STAT inhibitors to the skin of an individual in need thereof, comprising administering an effective amount of the formulation of claim 1.

* * * * *